United States Patent
Andrews et al.

(10) Patent No.: US 12,083,195 B2
(45) Date of Patent: Sep. 10, 2024

(54) MICROPARTICLES OF CELLULOSE NANOCRYSTALS WITH PIGMENT NANOPARTICLES BOUND THERETO AND METHOD OF PRODUCTION THEREOF

(71) Applicant: ANOMERA INC., Montréal (CA)

(72) Inventors: Mark P. Andrews, Westmount (CA); Timothy Morse, Toronto (CA); Monika Rak, Montreal (CA); Mary Bateman, St. Lazare (CA)

(73) Assignee: ANOMERA INC., Québec (CA)

( * ) Notice: Subject to any disclaimer, the term of this patent is extended or adjusted under 35 U.S.C. 154(b) by 0 days.

(21) Appl. No.: 17/419,524

(22) PCT Filed: May 6, 2020

(86) PCT No.: PCT/CA2020/050604
§ 371 (c)(1),
(2) Date: Jun. 29, 2021

(87) PCT Pub. No.: WO2020/227815
PCT Pub. Date: Nov. 19, 2020

(65) Prior Publication Data
US 2022/0040053 A1  Feb. 10, 2022

Related U.S. Application Data

(60) Provisional application No. 62/846,302, filed on May 10, 2019.

(51) Int. Cl.
*A61K 8/02* (2006.01)
*A61K 8/73* (2006.01)
*A61Q 1/12* (2006.01)

(52) U.S. Cl.
CPC ............ *A61K 8/0275* (2013.01); *A61K 8/731* (2013.01); *A61Q 1/12* (2013.01); *A61K 2800/412* (2013.01); *A61K 2800/413* (2013.01); *A61K 2800/43* (2013.01); *A61K 2800/621* (2013.01); *A61K 2800/622* (2013.01)

(58) Field of Classification Search
None
See application file for complete search history.

(56) References Cited

U.S. PATENT DOCUMENTS

| | | | | |
|---|---|---|---|---|
| 2009/0311295 A1* | 12/2009 | Mathiowitz | ............... | A61K 8/11 264/4.6 |
| 2010/0037955 A1* | 2/2010 | Carlini | ................. | C09D 17/003 977/773 |
| 2012/0244357 A1* | 9/2012 | Leung | ..................... | C08B 15/04 977/773 |
| 2019/0002700 A1* | 1/2019 | Andrews | ................ | A61K 8/027 |

FOREIGN PATENT DOCUMENTS

| | | |
|---|---|---|
| CN | 105166862 A | 12/2015 |
| JP | 2011037812 A | 2/2011 |
| WO | 2016015148 A1 | 2/2016 |
| WO | 2017091893 A1 | 6/2017 |
| WO | 2018100065 A1 | 6/2018 |

OTHER PUBLICATIONS

International Search Report (PCT/ISA/210) and Written Opinion (PCT/ISA/237) mailed on Jul. 17, 2020, by the Canadian Patent Office as the International Searching Authority for International Application No. PCT/CA2020/050604.
Auvinen, S. et al."Refractive Index Functions of TiO2Nanoparticles" The Journal of Physical Chemistry C, 2013, vol. 117, pp. 3503-3512.
Davis, K. et al." Quantitative Measurement of Ligand Exchange on Iron Oxides viaRadiolabeled Oleic Acid" Langmuir, 2014, 8 pages.
Levdik, Y."IR Study of Analytical and Structural Low-Substituted Methylcellulose Films" 1965, pp. 269-272.
Makarova, O. V. et al."Surface Modification of TiO2Nanoparticles For Photochemical Reduction of Nitrobenzene" Environmental Science & Technology, vol. 34, No. 22, 2000, pp. 4797-4803.
Martakov, I. S. et al."Interaction of cellulose nanocrystals with titanium dioxide andpeculiarities of hybrid structures formation" J Sol-Gel Sci Technol, 2018, vol. 88, pp. 13-21.
Moser, J. et al." Surface Complexation of Colloidal Semiconductors Strongly Enhances Interfacial Electron-Transfer Rates" Langmuir, 1991, vol. 7, pp. 3012-3018.
Tunesi, S. et al."Influence of ChemIsorption on the Photodecomposition of Salicylic Acid and Related Compounds Using Suspended TiO, Ceramic Membranes" J. Phys. Chem., 1991, vol. 95, pp. 3399-3405.
Bohren, C. F. et al."Absorption and Scattering of Light by Small Particles" Wiley-VCH Verlag GmbH & Co. KGaA, 534 pages.
Extended European Search Report dated Oct. 25, 2022, issued by the European Patent Office in corresponding European Application No. 20806006.1—1109, (45 pages).

(Continued)

*Primary Examiner* — David J Blanchard
*Assistant Examiner* — Sarah J Chickos
(74) *Attorney, Agent, or Firm* — BUCHANAN, INGERSOLL & ROONEY PC

(57) ABSTRACT

Microparticles comprising carboxylated, sulfated, or phosphated cellulose nanocrystals (CNCs) and pigment nanoparticles are provided. In these particles, the cellulose nanocrystals and the pigment nanoparticles are agglomerated together thereby forming said microparticle, and wherein the pigment nanoparticles are bound to the surface of the cellulose nanocrystals. Cosmetic preparations comprising these microparticles are also provided. Finally, a method for producing the microparticles is provided. The method comprises the steps of a) producing an aqueous suspension of carboxylated, sulfated, or phosphated CNCs with pigment nanoparticles bound thereto; and b) drying said aqueous suspension to produce the microparticles.

21 Claims, 13 Drawing Sheets

(56) References Cited

OTHER PUBLICATIONS

Polyphenols in Human Health and Disease, vol. 2, 2014, pp. 923-941.
Biochrome Defintion & Meaning, Merriam-Webster, 11 Pages.
Anthocyanidins and anthocyanins: colored pigments as food, pharmaceutical ingredients, and the potential health benefits, dated Aug. 13, 2017, 37 pages.

* cited by examiner

MICROPARTICLES OF CELLULOSE NANOCRYSTALS WITH PIGMENT NANOPARTICLES BOUND THERETO AND METHOD OF PRODUCTION THEREOF

CROSS REFERENCE TO RELATED APPLICATIONS

This application claims benefit, under 35 U.S.C. § 119(e), of U.S. provisional application Ser. No. 62/846,302, filed on May 10, 2019. This application is a National Stage Application of PCT/CA2020/050604, filed on May 6, 2020. All documents above are incorporated herein in their entirety by reference.

FIELD OF THE INVENTION

The present invention relates to microparticles of cellulose nanocrystals and to a method for producing said microparticles. More specifically, the present invention is concerned with microparticles of agglomerated carboxylated, sulfated or phosphated cellulose nanocrystals that have pigment nanoparticles bound thereto.

BACKGROUND OF THE INVENTION

Colors for cosmetics come in many varieties. These colors are divided among dyes and pigments. Because the cosmetics industry is moving towards natural pigments, there is a need for colors that are derived from natural sources—natural pigments and dyes.

Dyes and pigments are used to add a color to, or to change the color of, something. They are ubiquitous in the textile, pharmaceutical, food, cosmetics, plastics, paint, ink, photographic and paper industries. Dyes are colored substances that are soluble and dispersible at the molecular level in a liquid medium like water or an organic solvent. They impart color by selective absorption of light. The color expressed by a dye is a complex function of its molecular structure, concentration in the medium/host, pH, refractive index, physico-chemical interaction with a solid or fluid host (material like cotton, polymer, cosmetic or paint formulation), wavelength of light, and optical response, if the latter is altered by the host.

Pigments are particulate organic or inorganic finely divided solids that may be white, or black or colored. Pigments are insoluble in the fluid vehicle or medium in which they are suspended. Pigment color depends not only on the factors that affect the color of dyes, but also on the chemical composition of the pigment, particle size, particle size distribution, particle shape, crystal structure and concentration. Whereas the color of a dye is determined by the molecular structure of the dye through the absorption of light, the color of a pigment depends on absorption and scattering of light. Dyes usually provide brighter color than conventional pigments, but they typically are less light stable and less permanent. Dyes may have poor durability, poor heat and solvent stability, and high migration. In contrast, pigment colorants tend to be highly durable, heat stable, solvent resistant, lightfast, and migration fast. Pigments nevertheless tend to be hard to process and have poor color brilliance and strength.

Pigments are widely used in the cosmetic industry. Among the inorganic pigments are oxides of iron and chromium, various silicates like ultramarine and mica, and white semiconductors like titanium dioxide, and zinc oxide. These pigments are considered natural pigments, but while many inorganic pigments occur naturally, they may contain heavy metal and other contaminants. Therefore, all inorganic pigments for cosmetics are synthesized in a laboratory to ensure consumer safety.

To prepare a gamut of hues, pigments are often mixed together in powder form. For example, Sensient provides a brown hue called Unipure™ Brown LC887 by combining ratios of $Fe_2O_3 \cdot nH_2O$, $Fe_2O_3$ and $Fe_3O_4$. A blue hue called Unipure™ Blue LC685 is prepared by mixing ferric ammonium cyanide with talc. Organic and inorganic pigments can be combined to create hues. In all cases however, it can be difficult to reproducibly obtain a given hue by physically mixing powder pigments.

Furthermore, inorganic pigments have another disadvantage because they must be subjected to process-intensive milling in order to reduce or obtain small particle size and improve feel, especially for pressed and loose powders.

Generally, the surface of pigments must be modified to make them more compatible with cosmetic formulations and to offer additional benefits to enhance the sensation of the pigment during its application. To aid cosmetic formulation, provide functional properties and enhance the aesthetic experience, pigments are usually subjected to various kinds of surface treatments. These treatments alter the surface energy of the pigments in ways that improve formulation and the sensorial experience. Lauroyl lysine is one example of a surface treatment agent. It is an amino acid derivative obtained by combining lysine with lauric acid, a natural coconut fatty acid. Lauroyl lysine treatment creates a hydrophobic surface that favors enhanced pigment particle dispersion, increased wear properties and make-up with a wet feel on the skin. Treated pigments have improved resistance to breakage and dusting. The lauroyl lysine surface may be considered "natural", "pH balanced" and "compatible" with the skin.

Coated particles find application in eye shadow, facial powder, lipstick, foundation and blush powder. Alkylsilane coatings result from the reaction of organosilicon alkoxides with surface water and hydroxyl groups on pigment particles. Covalent bonds are formed among the silicon moieties and with the pigment surface following curing. The coating makes the pigment particles easily dispersible in mineral oils, esters and silicone fluids. They have very low surface tension, giving them excellent hydrophobicity and improved lipophilicity. Pigments treated with alkyl silane are more hydrophobic than methicone treated pigments, wet better in commonly utilized cosmetic oils and have lower oil absorption. In hydrous compact formulations, alkyl silane treatment imparts improved wetting to allow high pigment loading in powders. This confers a 'powdery' sensation upon application to the skin while maintaining a low melt viscosity for hot filling. The improvement in compatibility between the dispersed solids and the vehicle is a benefit in formulation of stick products including lipstick, eye shadows and foundations as the adverse effect of many inorganic pigments on stick structures is eliminated. These types of coatings are used to make W/O (water-in-oil) and O/W (oil-in-water) emulsions, water-proof mascara, long lasting lipstick and lip gloss.

Methicone is a poly(methylhydrosiloxane). The Si—H bond reacts with traces of water from the pigment surface and converts the Si—H bond to silanol (Si—OH), which ultimately condenses to make covalent Si—O pigment chemical bonds. The coating is highly hydrophobic and is tenaciously bound to the surface so that the coating resists shear. Pigments coated this way wet well in oils, particularly silicone oils. The skin feel is experienced as somewhat dry with enhanced slip and spreadability. It is preferred for pressed powder formulations. A drawback of such coating is that the methicone reaction must be taken to completion since the reaction evolves hydrogen gas. Methicone coated particles are suitable for color cosmetics: foundations, concealers, mascaras, lipsticks, eye shadow, and mousses. Dimethicone is actually poly(dimethylsiloxane). It is thought to bind to a pigment surface via the mechanism of hydrolysis, condensation and curing to create a Si—O pigment linkage. Surfaces treated with dimethicone are quite hydrophobic and have good slip and more lubricious feel. Pigments coated with dimethicone are useful in oil-based systems, which may be used for anhydrous products.

Other surface treating agents include Perfluorooctyl Triethoxysilane, Triethoxycaprylylsilane (and) Polyhydroxystearic Acid, Triethoxysilylethyl Polydimethylsiloxyethyl Dimethicone (and) Isopropyl Titanium Triisostearate, Triethoxycaprylylsilane (and) Polyhydroxystearic Acid, Ceramide NP (and) Stearic Acid (and) Cetearyl Alcohol (and) Phytosterols (and) Dimethicone, Isopropyl Titanium Triisostearate, Isopropyl Titanium Triisostearate (and) Sodium Lauroyl Aspartate (and) Zinc Chloride, Sodium Lauroyl Glutamate (and) Lysine (and) Magnesium Chloride, Magnesium Myristate, Methicone, Stearoyl Glutamic Acid, Jojoba Esters, Silica, Ethylene/Methacrylate Copolymer (and) Isopropyl Titanium Triisostearate (manufactured by KOBO) Polycaprylylsilsesquioxane, Stearyl Triethoxysilane, Triethoxycaprylsilane, Disodium Carboxyethyl Siliconate, Dimethicone PEG-3 Laurate, Trimethylsiloxysilicate, Diethylsiloxane (manufactured by GELEST), Galactoarabinan, Dimethicone, Alkyl Silane, DL-Lauroyl Lysine, Fluoropropyl Methicone, Magnesium Myristate, Green Tea, Mandarin Orange, Chamomile, Glycerin, Propanediol, Kaolin, Trimyristin (manufactured by COLORTECHNIQUES), Cyclopentasiloxane (and) Dimethicome (and) Disodium Stearoyl Glutamate (and) Aluminum Hydroxide, Disodium Stearoyl Glutamate, Hydrogenated Lecithin, Trimyristin (and) Hydrogenated Lecithin, Aluminum Dimyristate, Dimethicone, Dimethicone Glyceryl Rosinate (and) Octodocecyl Myristate, Methicone (manufactured by MYOSHI), Sodium Perfluorohexylethyl Phosphate, Perfluorooctyltriethoxysilane, Methicone/Hydrogen Dimethicone/Dimethicone, Acrylates/Dimethicone Copolymer, Triethoxycaprylylsilane, Pseudozyma Tsukubaensis/Olive Oil/Glycerin/Soy Protein Ferment, Magnesium Stearate, Hydrogenated Lecithin, Sodium Lauroyl Glutamate Lysine, Lauroyl Lysine, Sodium Lauroyl Aspartate Zinc Chloride Isopropyl Titanium Triisostearate, Silica, Microcrystalline Cellulose (manufactured by DAITO KASEI) Alkyl Silane, Polymethylhydrogen Siloxane (Methicone), Polymethylsiloxane (Dimethicone), Lauroyl Lysine (manufactured by Koel and Company), Dimethicone Copolyol, Alkyl Silane, Silicone, Perfluoro Alkane, Perfluoro Silane, Glutamate Cystine Arginine, Hydrogenated Lecithin, Natural Flower Wax, N-Lauroyl L-Lysine, and Sodium Glycerophosphate.

The coating methods described above are disadvantageous in that they require several additional steps after production of the pigment.

Another challenge is that the demand for cosmetic products that match the skin tone of consumers is rising with increasing product differentiation in the cosmetic and personal care industry. Skin tones vary in complex ways among human skin types. The cosmetics industry has attempted to address the challenge of matching skin tone by various means. Many involve the use of color charts or digital menus that allow the client to select combinations of tones and undertones. A more precise way to color match is to use a spectrophotometer that acts as a diagnostic platform to suggest particular color formulations. Such diagnostic platforms can make use of data from large beauty databases and combine the data with machine learning algorithms to personalize skin tone products. As much as these advances improve the accuracy of matching skin tone, the limited base of pigments does not provide the product differentiation that is crucial to the experience of the consumer or that can provide a competitive edge to cosmetics industry players.

Another challenge is due to the fact that the preference for colored materials among consumers has increased the adoption of nano-cosmetic pigments. In general, nanoscale ingredients can increase the perceived value of a product at point-of-sales. The cosmetic industry is well-known for personalization and customization with vast choices of make-up cosmetics to embrace the individuality of customers. Thus, there is high demand for individuality and personalization of products. Cosmetic product designers seek new ways to make their products unique. Pigments offer an opportunity to the cosmetic manufacturers for innovative and commercially attractive solutions. Moreover, advancements in nanotechnology are anticipated to develop innovative pigments. The class of so-called "effect pigments" creates lustrous, iridescent, and angle-dependent optical effects that are much sought after in the cosmetics industry. Synthetic fluorophlogopite mica platelets can be coated with titanium dioxide or iron oxides. Titanium dioxide-mica pigments are manufactured by hydrolysis of $TiOSO_4$ or by titration with $TiOCl_2$. $TiO_2$ is deposited as anatase or rutile. The interference color of these pigments depends on the thickness of the $TiO_2$ layer, which is typically nanoscale, i.e., in the range of 50-300 nm on both sides of the mica platelets. Iron oxide layers can be deposited on the mica from iron (II) sulfate or iron (III) chloride. Platelets are typically 100-200 nm thick and 5 to 100 micrometers in length. These pigments are therefore nanoscale in only the thickness dimension.

Because of the contrasting properties of dye and pigment colorants, there is incentive to improve the attributes of each class of these colorants by co-locating the most attractive features of both in a single particle. Accordingly, nano-colorants have emerged as a new class of colorants to take advantage of the contrasting properties between dyes and pigments. Nano-colorants are composites that may range in size from nanometers to micrometers and even larger. A definition of a nano-colorant is that the colorant—dye or pigment—is dispersed at the nanoscale in the composite. Conventionally, nano-colorants combine a dye in a suitable polymeric matrix. In this case, the objective is to integrate the chromatic properties and good processability of dyes and the durability of organic pigments in a single composite matrix, the polymer. Nano-colorants can be made by encapsulating dyes during mini-emulsion polymerization to yield dyed nanoscale polymer particles. They can also be prepared by the solution sol-gel method, or by intercalation in, or adsorption onto, nano-clay particles. The methods to make nano-colorants are complex, especially those requiring the use of dyes.

Nano-pigments are also a type of nano-colorant, but they are not without disadvantages. In cosmetics, nano-pigments are primarily derived from titanium dioxide ($TiO_2$) and zinc oxide (ZnO). They are used to protect the skin against the harmful effects of UVA and UVB radiation. Nanozinc oxide has not been permitted by the European Commission as a UV-filter. In the US both nano-$TiO_2$ and nano-ZnO are allowed. Despite the use of nano-$TiO_2$ and nano-ZnO in cosmetics, there is reluctance on the part of the industry to admit widespread use of nanoparticles into cosmetics. This is because knowledge of the impact of nanoparticles on human health and the ecosystem is still evolving.

The cosmetic and personal care industry is moving towards the creation of products that are "naturally sourced". This term is difficult to define, and the ISO group has approached the problem by defining a "natural index". The natural index is a value indicating the extent to which a cosmetic ingredient meets the definition of natural ingredients from ISO 16128-1:2016, clause 2. The value can be construed as varying between 0 and 1, where 1 can be interpreted as 100% natural (of "organic" origin). The ISO provisions are disputed because certification admits "natural ingredients" from genetically modified origins (GMOs), permits the use of petrochemical substances and offers an algorithm for calculating the natural index that can admit compositions of matter that are neither natural nor certified as organic. Nevertheless, the cosmetics industry is pressuring suppliers of ingredients to use sustainable manufacturing methods in the production of ingredients, to ensure a high natural index and to exclude GMO additives.

According to the invention of WO 2017/091893, the contents of which are incorporated by reference, a colored pigment comprising a cationic or anionic dye, a polycation and cellulose nanocrystals (CNCs) can be made by binding the dye to the polycation bound to the CNCs. This electrostatic binding interaction occurs at the molecular scale. The dyed CNCs are subsequently spray dried to yield a free-flowing powder, called the pigment. This method requires the use of cationic or anionic dye molecules. Moreover, the method requires the use of an oppositely charged (anionic or cationic) polyelectrolyte, adsorbed onto the surface of the nanocrystals, to bind the charged dye molecules.

There is also incentive to create new classes of pigments that are derived in whole or in part from renewable resources, sustainable manufacturing methods, green chemistry and green engineering processes, all with a focus on conscientious environmental practices. For example, the print industry uses environmentally friendly inks (EFIs) in some applications. In general, circular economies—ones that look at the complete life cycle of a product, including its recycling—are moving towards components of products that bring value in terms of sustainability coupled with performance. Despite the momentum in the cosmetics industry towards ingredients with higher naturality index, organic and inorganic pigments alone suffer from a low naturality index.

SUMMARY OF THE INVENTION

In accordance with the present invention, there is provided:

1. A microparticle comprising carboxylated, sulfated, or phosphated cellulose nanocrystals and pigment nanoparticles, wherein the cellulose nanocrystals and the pigment nanoparticles are agglomerated together thereby forming said microparticle, and wherein the pigment nanoparticles are bound to the surface of the cellulose nanocrystals.
2. The microparticle of item 1, wherein the microparticles are about 0.2 µm to about 20 µm in diameter, preferably the microparticles are at least about 0.2 µm; at least about 1 µm; at least about 2 µm; at least about 4 µm; or at least about 5 µm; and/or at most about 20 µm; at most about 15 µm; at most about 12 µm; or at most about 10 µm in diameter.
3. The microparticle of item 1 or 2, wherein the cellulose nanocrystals are about 2 nm to about 20 nm in diameter and about 80 nm to about 250 nm in length, preferably about 5 nm to about 10 nm in diameter and about 150 to about 200 nm in length.
4. The microparticle of any one of items 1 to 3, wherein the cellulose nanocrystals are carboxylated cellulose nanocrystals.
5. The microparticle of any one of items 1 to 4, wherein the pigment nanoparticles are between about 10 nm and about 1 micron in size, preferably at least about 10 nm, at least about 25 nm, or at least about 50 nm, and/or at most about 1 micron, at most about 500 nm, at most about 250 nm, at most about 200 nm, at most about 100 nm, at most about 75 nm, or at most about 50 nm in size.
6. The microparticle of any one of items 1 to 5, wherein the pigment nanoparticles are present in an amount of between about 0.1 wt % and about 75 wt % of the combined weight of the pigment nanoparticles and the cellulose nanocrystals, preferably in an amount of at least about 0.1 wt %; at least about 0.5 wt %; at least about 1 wt %; at least about 2 wt %; at least about 3 wt %; at least about 5 wt %; or at least about 10 wt %; and/or at most about 75 wt %; at most about 50 wt %; at most about 25 wt %; at most about 20 wt %; at most about 15 wt %; or at most about 13.5 wt % of the combined weight of the pigment nanoparticles and the CNCs.
7. The microparticle of any one of items 1 to 6, wherein the pigment nanoparticles are inorganic pigment nanoparticles, organic pigment nanoparticles, or a mixture thereof.
8. The microparticle of any one of items 1 to 7, wherein the pigment nanoparticles are organic pigment nanoparticles.
9. The microparticle of item 8, wherein organic pigment nanoparticles are nanoparticles of least one of FD&C Blue 1 Aluminum Lake, D&C Blue 4 Aluminum Lake, D&C Green 3 Aluminum Lake, D&C Orange 4 Aluminum Lake, D&C Orange 5 Aluminum Lake, D&C Orange 5 Aluminum/Zirconium Lake, D&C Orange 5 Zirconium Lake, D&C Red 4 Aluminum Lake, D&C Red 6 Barium Lake, D&C Red 6 Aluminum Lake, D&C Red 6 Barium/Strontium Lake, D&C Red 6 Potassium Lake, D&C Red 6 Strontium Lake, D&C Red 7 Barium Lake, D&C Red 7 Aluminum Lake, D&C Red 7 Calcium/Strontium Lake, D&C Red 7 Zirconium Lake, D&C Red 7 Strontium Lake, D&C Red 21 Aluminum Lake, D&C Red 27 Aluminum Lake, D&C Red 27 Aluminum/Titanium/Zirconium Lake, D&C Red 27 Barium Lake, D&C Red 27 Calcium Lake, D&C Red 27 Zirconium Lake, D&C Red 28 Al Lake, D&C Red 30 Aluminum Lake, D&C Red 30 Talc Lake, D&C Red 33 Aluminum Lake, D&C Red 34 Aluminum Lake, D&C Red 36 Aluminum Lake, D&C Red 36 Zirconium Lake, F&DC Red 40 Aluminum Lake (Allura Red), F&DC Red 40 Calcium Lake, FD&C Yellow 5 Aluminum Lake, FD&C Yellow 5 Zirconium Lake, FD&C Yellow 6 Aluminum Lake, or D&C Yellow 10 Aluminum Lake.
10. The microparticle of any one of items 1 to 7, wherein the pigment nanoparticles are inorganic pigment nanoparticles.
11. The microparticle of item 10, wherein the inorganic pigment nanoparticles are metal oxide nanoparticles.

12. The microparticle of item 10 or 11, wherein the inorganic pigment nanoparticles are nanoparticles of an iron oxide, a chromium oxide, an ultramarine, a manganese pigment, or a titanium dioxide.
13. The microparticle of any one of items 10 to 12, wherein the inorganic pigment nanoparticles are titanium dioxide nanoparticles, black magnetite ($Fe_3O_4$) nanoparticles, or ultramarine nanoparticles.
14. The microparticle of any one of items 10 to 13, wherein the inorganic pigment nanoparticles are black magnetite nanoparticles.
15. The microparticle of items 14, wherein the black magnetite nanoparticles have a particle size between about 10 nm and about 500 nm in size, preferably a particle size between about 50 nm and about 100 nm.
16. The microparticle of items 14 or 15, wherein the black magnetite nanoparticles have a surface area of greater than 60 $m^2/g$.
17. The microparticle of any one of items 14 to 16, wherein the black magnetite nanoparticles are at a concentration from about 0.1% w/w to about 50% w/w, based on the combined weight of the cellulose nanocrystals and the black magnetite nanoparticles.
18. The microparticle of any one of items 1 to 17, further comprising dyed cellulose nanocrystals of at least one hue.
19. The microparticle of item 18, wherein the dyed cellulose nanocrystals comprising:
    cellulose nanocrystals having a surface charge,
    optionally one or more polyelectrolyte layers with alternating charges adsorbed on top of each other on the cellulose nanocrystals, the polyelectrolyte layer closest to the cellulose nanocrystals having a charge opposite the surface charge of the cellulose nanocrystals, and
    at least one organic dye having a charge,
    wherein:
    A) when the charge of the organic dye is opposite the surface charge of the cellulose nanocrystals,
        1) the organic dye is directly adsorbed on the surface of the cellulose nanocrystals without intervening polyelectrolyte layers, or
        2) the organic dye is adsorbed on an even number of polyelectrolyte layers with alternating charges, and
    B) when the charge of the organic dye is the same as the surface charge of the cellulose nanocrystals, the organic dye is adsorbed on an odd number of polyelectrolyte layers with alternating charges.
20. The microparticle of item 18 or 19 wherein the dyed cellulose nanocrystals comprise Citrus red 2, FD&C Blue 1, D&C Blue 4, D&C Green 3, D&C Green 4, D&C Green 5, D&C Green 6, D&C Green 8, D&C Orange 4, D&C Orange 5, D&C Orange 10, D&C Orange 11, FD&C Red 4, D&C Red 6, D&C Red 7, D&C Red 21, D&C Red 27, D&C Red 28, D&C Red 30, D&C Red 31, D&C Red 33, D&C Red 34, D&C Red 36, D&C Red 39, FD&C Red 40, D&C Red 40, D&C Violet 2, FD&C Yellow 5, FD&C Yellow 6, D&C Yellow 10, preferably FD&C yellow 5 or FD&C Red 40, and more preferably FD&C Red 40.
21. A cosmetic preparation comprising the microparticles of any one of items 1 to 20.
22. A method for producing the microparticles of any one of items 1 to 20, the method comprising the steps of:
    a. producing an aqueous suspension of the carboxylated, sulfated, or phosphated CNCs with pigment nanoparticles bound thereto; and
    b. drying said aqueous suspension to produce the microparticles.
23. The method of item 22, wherein step a) comprises the steps of producing an aqueous suspension of the carboxylated, sulfated, or phosphated CNCs and then adding the pigment nanoparticles to the aqueous suspension.
24. The method of item 22 or 23, wherein step b) comprises spray-drying the suspension.

DETAILED DESCRIPTION OF THE INVENTION

Figure 1A:
FIGS. 1a-1b are a) an SEM image and b) an element-specific SEM image of the microparticles of Example 1: 13.5% $Fe_3O_4$ in CNC.

There is provided a microparticle comprising carboxylated, sulfated, or phosphated cellulose nanocrystals (CNCs) and pigment nanoparticles, wherein the cellulose nanocrystals and the pigment nanoparticles are agglomerated together thereby forming said microparticle, and wherein the pigment nanoparticles are bound to the surface of the cellulose nanocrystals. There is also provided a method for producing said microparticles.

The present inventors discovered that a microparticle can be prepared by combining cellulose nanocrystals with pigment nanoparticles as described below. In doing so, the inventors have found a way to make pigment particles of micrometer dimensions (at least 0.2 microns in size) comprising cellulose nanocrystals and pigment nanoparticles.

These microparticles make for desirable microscale pigments, as the benefits of using pigment nanoparticles are achieved (such as more vibrant colors) while avoiding problems that may be associated with such nanoparticle pigments (as said pigment nanoparticles are bound to the CNCs). For example, the pigment nanoparticles that are part of the microparticles of the invention do not wash off when exposed to water or organic solvents and are therefore color-fast.

This discovery creates new opportunities to design nano-pigments with new optical properties, without the uncertainty of shedding free nanoscale pigments.

In addition, as will be discussed below and as shown in the Examples, the microparticles of the invention surprisingly offer the ability to prepare a vast range of skin tones using only $Fe_3O_4$ nanoparticles combined at various ratios with CNC.

Microparticles Comprised of CNCs with Pigment Nanoparticles Bound Thereto

In a first aspect of the invention, a microparticle comprising carboxylated, sulfated, or phosphated cellulose nanocrystals and pigment nanoparticles is provided.

In this microparticle, the pigment nanoparticles are bound to the surface of the CNCs. Indeed, the present inventors have found that it is possible to produce microparticles by a spray-drying process during which the pigment nanoparticles attach themselves to the nanocrystals so they have a dramatically reduced likelihood of being washed out of the microparticles. Accordingly, the pigment nanoparticles can be located at the surface, near subsurface, and/or in the interior of the microparticle, depending on the location of the CNC they are bonded to. The bonding occurring during spray-drying between the pigment nanoparticles and the CNCs can be covalent or noncovalent based on hydrogen bonding, ionic bonding, van der Waals interactions, hydrophobic interactions, or combinations of noncovalent interactions. In preferable embodiments, the bonding is noncovalent.

In the microparticle of the invention, the cellulose nanocrystals and the pigment nanoparticles are agglomerated together and thus form said microparticle. This means that the physical structure of the microparticles is provided by the agglomerated CNCs and pigment nanoparticles. In other words, it is the CNCs and the pigment nanoparticles that form the structure of the microparticles, that are responsible for the physical integrity of the structure.

In embodiments, the microparticle of the invention consists of the cellulose nanocrystals and the pigment nanoparticles.

Typically, the microparticles of the present invention are about 0.2 μm to about 20 μm in diameter. In embodiments, the microparticles are at least about 0.2 μm; at least about 1 μm; at least about 2 μm; at least about 4 μm; or at least about 5 μm; and/or at most about 20 μm; at most about 15 μm; at most about 12 μm; or at most about 10 μm in diameter.

The microparticles can assume different morphologies when spray dried. The morphologies can vary from approximately spherical to globular to deformed disc shapes. Spherical particles tend to roll on the skin and offer a smooth feel. Globular to deformed disc shapes scatter light differently than do spheres, and the optical scattering that results confers different outcomes in diffuse reflectance that may be desirable for some cosmetic applications. For example, various shapes are shown in Examples 1, 4, 5, 8, and even Comparative Example 7 (discussed below). The shapes depend in complex ways on the spray drying conditions and on the composition of the feed to make the microparticle. For example, two different particle shapes—one spherical and one globular—can emerge when 13.5% $Fe_3O_4$ is spray dried with CNC to make microparticles (see Example 1 below). In addition, rough globular microparticles can be produced when 1% $Fe_3O_4$ and 0.5% Red 40 are spray dried to make CNC microparticles (see Example 4 below). Furthermore, combining 5% Ultramarine Blue with CNC can produce collapsed concave disc-like microparticles together with smaller microparticles upon spray drying (see Example 5 below). Therefore, at fixed spray drying conditions, the feed composition can affect microparticle morphology. Changes in morphology can produce new types pigment particle powders with desirable skin feel (e.g. dry vs creamy) and desirable optical properties, like greater vibrancy and saturation.

The microparticles of the invention are typically free from each other (i.e. detached from one another).

In embodiments, the microparticles are in the form of a free-flowing powder.

The Cellulose Nanocrystals

The CNCs typically have dimensions in diameter of 2 to 20 nm and in length, 80-250 nm, for example dimensions in diameter of 5 to 10 nm and in length, 150-200 nm.

As mentioned, the CNCs are carboxylated, sulfated, or phosphated CNCs. It is believed that these surface functional groups allow the pigment nanoparticles to bind to the CNCs. The modes of binding can be described below. As mentioned, in embodiments, the bonding is noncovalent and can, for example, involve chelation or hydrogen bonded interactions.

Carboxylated CNCs are at least partially surface oxidized and thus bear carboxyl (—C(=O)OH)/carboxylate (—C(=O)O⁻) groups on their surface. Sulfated CNCs are at least partially surface sulfated and thus bear sulfate ester hydroxyl (—CH₂—O—S(=O)₂(OH)) or sulfate ester ion (—CH₂—O—S(=O)₂(O⁻)) groups on their surface, typically at the C6 position on the cellulose. Phosphated CNCs are at least partially surface phosphated, and thus bear phosphate half-ester (—CH₂—O—P(=O)(O⁻)₂) groups on their surface. The carboxylated, sulfated, or phosphated CNCs can be produced using any known technique in the art.

In preferred embodiments, the cellulose nanocrystals are carboxylated cellulose nanocrystals. Such carboxylated CNCs can be produced as described in WO2016015148, which is incorporated herein by reference.

Dyed Cellulose Nanocrystals

In embodiments, the microparticle of the present invention may further comprise dyed cellulose nanocrystals of at least one hue. These dyed cellulose nanocrystals, including preferred embodiments thereof, are as defined in WO 2017/091893, which is incorporated herein by reference.

In embodiments, these dyed cellulose nanocrystals comprise CNC having a surface charge, optionally one or more polyelectrolyte layers with alternating charges adsorbed on top of each other on the CNC, the polyelectrolyte layer closest to the CNC having a charge opposite the surface charge of the CNC, and at least one organic dye having a charge, wherein: A) when the charge of the organic dye is opposite the surface charge of the CNC, 1) the organic dye is directly adsorbed on the surface of the CNC without intervening polyelectrolyte layers, or 2) the organic dye is adsorbed on an even number of polyelectrolyte layers with alternating charges, and B) when the charge of the organic dye is the same as the surface charge of the CNC, the organic dye is adsorbed on an odd number of polyelectrolyte layers with alternating charges.

Said organic dye may be any dye known in the art, and may be chosen depending on the desired hue and other properties of the microparticle. In embodiments, the dye can be Citrus red 2, FD&C Blue 1, D&C Blue 4, D&C Green 3, D&C Green 4, D&C Green 5, D&C Green 6, D&C Green 8, D&C Orange 4, D&C Orange 5, D&C Orange 10, D&C Orange 11, FD&C Red 4, D&C Red 6, D&C Red 7, D&C Red 21, D&C Red 27, D&C Red 28, D&C Red 30, D&C Red 31, D&C Red 33, D&C Red 34, D&C Red 36, D&C Red 39, FD&C Red 40, D&C Red 40, D&C Violet 2, FD&C Yellow 5, FD&C Yellow 6, D&C Yellow 10. In embodiments, the dye is molecular dye FD&C yellow 5 or FD&C Red 40, preferably FD&C Red 40.

In preferred embodiments, the microparticle of the present invention comprises CNCs (undyed), magnetite ($Fe_3O_4$) nanoparticles (used as pigment nanoparticles, preferably 1 wt %) as well as the red-dyed CNCs called "Red 40-$CNC^+$", prepared as described in WO 2017/091893 or according to Example 4 herein below (with D&C Red dye 40 used as the dye) (preferably 0.5 wt %). For example, a brown tone can be warmed in tone by combining 1 wt % nano-$Fe_3O_4$ with an aqueous suspension of CNC and 0.5 wt % of Red 40-$CNC^+$, prepared according to WO 2017/091893 or according to Example 4 hereinbelow (with FD&C Red dye 40 used as the dye). When spray dried, a free-flowing brown powder is produced (as discussed in Example 4 hereinbelow).

The Pigment Nanoparticles

The pigment nanoparticles can be inorganic pigment nanoparticles, organic pigment nanoparticles, or a mixture thereof. In preferred embodiments, the pigment nanoparticles are inorganic pigment nanoparticles. Examples and preferred examples of both inorganic and organic pigment nanoparticles are provided below.

The properties of pigment nanoparticles are determined inter alio by chemical composition, particle size, particle size distribution, particle shape, concentration, and crystal structure. Accordingly, these properties of the pigment nanoparticles can be selected and modified depending on the desired qualities of the pigment nanoparticles and the desired qualities of the resulting microparticle.

Typically, the size of pigment nanoparticles depends on the method of production. In embodiments, the pigment particles used in the present invention are between about 10 nm and about 1 micron in size. In preferred embodiments, the pigment nanoparticles are at least about 10 nm, at least about 25 nm, or at least about 50 nm, and/or at most about 1 micron, at most about 500 nm, at most about 250 nm, at most about 200 nm, at most about 100 nm, at most about 75 nm, or at most about 50 nm in size.

It is to be understood that the preferred size of the pigment nanoparticles may depend on the pigment nanoparticles used. For example, using ultramarine blue pigment particles of 1 micron in size allows for the producing of an effective pigment (see Examples 5 and 6), probably because they are broken into smaller particles during the manufacture of the microparticles of the invention. Conversely, $Fe_3O_4$ particles of 1 micron in size do not allow for the producing of an effective pigment (see Comparative Example 7).

In general, a narrower size distribution is desired because the final composition of the pigment microparticle will better reflect the composition of the starting suspension used to make the pigment particles.

In the invention, the shape of the pigment nanoparticles is not particularly limited. A skilled person will know to select an appropriate shape to suit his/her needs. Indeed, it is well known to those versed in the art that the extinction spectrum of nanoparticles (including the spectral reflectance) depends on the nanoparticle shape, composition, orientation, as well as the refractive index of the host.

In the invention, the crystalline phase of the pigment nanoparticles (when the pigment is crystalline) is also not particularly limited. A skilled person will know to select an appropriate crystalline phase to suit her/his needs. Indeed, it is well-known that modifying the crystal structure of the pigment nanoparticles will generally affect the properties thereof, thereby affecting the properties of the resulting microparticle—see for example anatase, rutile and brookite below.

The amount of pigment nanoparticles may vary depending on the desired effect (hue or other). The skilled person would understand that the quantities of each pigment will influence the properties of the resulting microparticle. In embodiments, the pigment nanoparticles are present in an amount of between about 0.1 wt % and about 75 wt % of the combined weight of the pigment nanoparticles and the CNCs. In embodiments, the pigment nanoparticles are present in an amount of at least about 0.1 wt %; at least about 0.5 wt %; at least about 1 wt %; at least about 2 wt %; at least about 3 wt %; at least about 5 wt %; or at least about 10 wt %; and/or at most about 75 wt %; at most about 50 wt %; at most about 25 wt %; at most about 20 wt %; at most about 15 wt %; or at most about 13.5 wt % of the combined weight of the pigment nanoparticles and the CNCs.

With respect to the hue of the pigments, it should be stated that pigments (as well as dyes) are sometimes characterized by their Color Index International (CI number).

The pigments chosen will determine the properties of the resulting microparticle, including the hue thereof. The skilled person would understand that various pigments and combinations of pigments can be chosen depending on the desired hue (or any other property) of the microparticle.

Organic Pigment Nanoparticles

In embodiments, the pigment nanoparticles are organic pigment nanoparticles. The organic pigment can include any organic pigment known in the art that can exist in nanoscale form and bind to the CNCs.

The number of organic pigments is large. These are described in various monographs. Some classes of organic pigments are monoazo yellow and orange, diazo, beta-naphthol, naphthol red, benzimidazolone, isoindolinone and isoindoline, polycyclics, phthalocyanines, quinacridones, perylene and perinone, diketopyrrolo-pyrrole, thioindigo, anthroquinone, anthrapyrimidine, flavanthrone, pyranthrone, anthanthrone, dioxazine, triarylcarbonium, and quinophthalone. These are used across a broad range of industries like paints, coatings and plastics, and in restricted cases, in pharmaceuticals and cosmetics. Lake pigments (lakes, for short) are a subset of organic pigments. Lake pigments are defined by the FDA as aluminum salts of FD&C water soluble dyes bound to a substratum of alumina. Lakes are prepared by adsorbing the sodium or potassium salt of a dye onto hydrated alumina. The "D&C" modifier is provided to the name of a lake prepared by extending the aluminum salt of an FD&C dye upon a substratum other than alumina. Examples of FD&C and D&C lakes are FD&C Blue 1 Aluminum Lake, D&C Blue 4 Aluminum Lake, D&C Green 3 Aluminum Lake, D&C Orange 4 Aluminum Lake, D&C Orange 5 Aluminum Lake, D&C Orange 5 Aluminum/Zirconium Lake, D&C Orange 5 Zirconium Lake, D&C Red 4 Aluminum Lake, D&C Red 6 Barium Lake, D&C Red 6 Aluminum Lake, D&C Red 6 Barium/Strontium Lake, D&C Red 6 Potassium Lake, D&C Red 6 Strontium Lake, D&C Red 7 Barium Lake, D&C Red 7 Aluminum Lake, D&C Red 7 Calcium/Strontium Lake, D&C Red 7 Zirconium Lake, D&C Red 7 Strontium Lake, D&C Red 21 Aluminum Lake, D&C Red 27 Aluminum Lake, D&C Red 27 Aluminum/Titanium/Zirconium Lake, D&C Red 27 Barium Lake, D&C Red 27 Calcium Lake, D&C Red 27 Zirconium Lake, D&C Red 28 Al Lake, D&C Red 30 Aluminum Lake, D&C Red 30 Talc Lake, D&C Red 33 Aluminum Lake, D&C Red 34 Aluminum Lake, D&C Red 36 Aluminum Lake, D&C Red 36 Zirconium Lake, F&DC Red 40 Aluminum Lake (Allura Red), F&DC Red 40 Calcium Lake, FD&C Yellow 5 Aluminum Lake, FD&C Yellow 5 Zirconium Lake, FD&C Yellow 6 Aluminum Lake, D&C Yellow 10 Aluminum Lake.

In the microparticle of the present invention, the organic pigment (if present) can include any organic pigment known in the art that can exist in nanoscale form and bind to the CNCs. In embodiments, the organic pigment can include any of the organic pigments listed above.

In preferred embodiments, the organic pigment is at least one of FD&C Blue 1 Aluminum Lake, D&C Blue 4 Aluminum Lake, D&C Green 3 Aluminum Lake, D&C Orange 4 Aluminum Lake, D&C Orange 5 Aluminum Lake, D&C Orange 5 Aluminum/Zirconium Lake, D&C Orange 5 Zirconium Lake, D&C Red 4 Aluminum Lake, D&C Red 6 Barium Lake, D&C Red 6 Aluminum Lake, D&C Red 6 Barium/Strontium Lake, D&C Red 6 Potassium Lake, D&C Red 6 Strontium Lake, D&C Red 7 Barium Lake, D&C Red 7 Aluminum Lake, D&C Red 7 Calcium/Strontium Lake, D&C Red 7 Zirconium Lake, D&C Red 7 Strontium Lake, D&C Red 21 Aluminum Lake, D&C Red 27 Aluminum Lake, D&C Red 27 Aluminum/Titanium/Zirconium Lake, D&C Red 27 Barium Lake, D&C Red 27 Calcium Lake, D&C Red 27 Zirconium Lake, D&C Red 28 Al Lake, D&C Red 30 Aluminum Lake, D&C Red 30 Talc Lake, D&C Red 33 Aluminum Lake, D&C Red 34 Aluminum Lake, D&C Red 36 Aluminum Lake, D&C Red 36 Zirconium Lake, F&DC Red 40 Aluminum Lake (Allura Red), F&DC Red 40 Calcium Lake, FD&C Yellow 5 Aluminum Lake, FD&C Yellow 5 Zirconium Lake, FD&C Yellow 6 Aluminum Lake, D&C Yellow 10 Aluminum Lake.

Inorganic Pigment Nanoparticles

In embodiments, the pigment nanoparticles are inorganic pigment nanoparticles. The inorganic pigment can include any inorganic pigment known in the art that can exist in nanoscale form and bind to the CNCs. Preferred inorganic pigments includes metal oxides.

Examples of inorganic pigments that can be used in the microparticles of the invention are provided in the next paragraphs.

Iron oxide pigments (CI 77489, CI 77491, CI 77492, CI 77499) are yellow, red or black. Yellow iron oxide is iron (III) oxide hydroxide, also known as ferric acid, hydrated iron oxide. Red iron oxide is iron (III) oxide, also known as ferric oxide, hematite or maghemite. Black iron oxide is iron (II, III), magnetite ($Fe_3O_4$). These find uses in all types of colour cosmetics, including foundations, face powders, lipsticks and eye shadows. A disadvantage of iron oxide pigments is that they have a very narrow color spectrum, being largely limited to orange-red-red-brown hues. Other types of iron oxide include wüstite (FeO), alpha- and beta- phase hematite ($\alpha$-$Fe_2O_3$, $\beta$-$Fe_2O_3$), gamma phase maghemite ($\gamma$-$Fe_2O_3$), epsilon ferrite ($\varepsilon$-$Fe_2O_3$), iron(II) hydroxide ($Fe(OH)_2$), iron(III) hydroxide ($Fe(OH)_3$), goethite ($\alpha$-FeOOH), akaganéite ($\beta$-FeOOH), $FeO_{0.833}(OH)_{1.167}Cl_{0.167}$, lepidocrocite ($\gamma$-FeOOH), feroxyhyte ($\delta$-FeOOH), and other oxides of stoichiometry, $Fe_4O_5$, $Fe_5O_6$, $Fe_5O_7$, $Fe_{13}O_{19}$ and $Fe_{25}O_{32}$. In preferred embodiments, the crystalline phase of the pigment iron oxide particles can be that of magnetite ($Fe_3O_4$), which is black, maghemite ($\gamma$-$Fe_2O_3$), hematite ($\alpha$-$Fe_2O_3$), wüstite ($Fe_{1-x}O$), or combinations thereof.

Chromium oxides are trivalent Cr(III) compounds that provide hues of green ranging from dull olive green, to blue-green, and bright green. Chromium oxides find use in most categories of cosmetic preparations but are prohibited for use in lip products in the USA. Chromium Oxide Green (CI 77288, $Cr_2O_3.2H_2O$) is a flat, matte, medium green pigment. It is widely used in soap-making as a non-bleeding color. It is also used extensively in cosmetics to adjust hues in foundations, blushes, bronzers and similar products, when they conform to FDA specifications. In the USA, chromium oxide green is approved for eyes and face products but not allowed for lip products. In the EU it is approved for lips, eyes and face products. The safety and ecotoxicity of chromium oxides remain in question. A disadvantage of chromium oxide pigments is that they have a very narrow color spectrum and that their green colors are not vibrant.

Ultramarines (CI 77007) range from bright blue to violet, pink and green. Ultramarine blue is based on the blue cubic mineral called lazurite. Lazurite is an aluminosilicate zeolite with the sodalite structure, which is a complex sulfur-containing sodium-silicate ($Na_{8-10}Al_6Si_6O_{24}S_{2-4}$). The blue color is due to the S3-minus radical anion having an unpaired electron. Synthetic ultramarine is more vibrant in color than natural ultramarine because its particles are smaller and more uniform and therefore diffuse light more evenly than the particles in natural ultramarine. Synthetic red, green and purple ultramarine pigments are known. Synthetic ultramarine typically requires a two-step process involving temperatures greater than 700° C. followed by reducing conditions between 350 and 450° C. A by-product of the production of ultramarine is sulfur dioxide which, because it is an environmental pollutant, must be removed from flue gas. Ultramarines may be safely used for coloring cosmetics and personal care products, including products intended for use in the area of the eye, when they conform to FDA specifications. Ultramarines are not allowed to be used in lipstick in the USA. In Europe ultramarines are approved for use in all cosmetics without restriction.

Purple hues can also be based on manganese violet (CI 77742); the pigment is ammonium manganese (III) pyrophosphate. Manganese violet pigment is used in the formulation of makeup, hair coloring products, bath products, nail polish and skin care products. Manganese violet may be safely used for coloring cosmetics and personal care products, including products intended for use on the lips and products intended for use in the area of the eye, when it conforms to FDA specifications.

Titanium dioxide can also be used as a pigment.

In preferred embodiments, the inorganic pigment nanoparticles are titanium dioxide nanoparticles, black magnetite ($Fe_3O_4$) nanoparticles, or ultramarine nanoparticles. These pigments are discussed in more detail below.

Titanium Dioxide Nanoparticles

In preferred embodiments, the inorganic pigment nanoparticles are titanium dioxide nanoparticles.

In embodiments, the crystalline phase of the pigment $TiO_2$ nanoparticles can be anatase, rutile, brookite, or combinations thereof. Anatase, rutile and Brookite have different refractive indices and different electronic absorption properties. Therefore, including one or more of the phases of $TiO_2$ will affect the optical properties of the final pigment particle. In preferred embodiments, the crystal structure of the pigment nanoparticles is rutile, which is preferable in cosmetics.

Choosing a pigment with SPF boosting properties, like $TiO_2$, will provide the resulting microparticle with SPF boosting properties. Indeed, as shown in Example 8, it was surprisingly discovered that the titanium dioxide nanoparticles, when spray-dried with carboxylated CNC, yielded microparticles of CNC that contained titanium dioxide nanoparticles bound to the surface, near subsurface, and most probably, to the interior of the microparticle. It was also discovered that the resulting microparticle imparted an SPF booster effect. The combination of the two nanoscale materials, $TiO_2$ nanoparticles and cellulose nanocrystals, creates a microparticle that is attractive as a cosmetic ingredient because it enhances whitening and/or coverage. The microparticles also exhibit a soft feel that is superior to the feel of conventional pigments, like $TiO_2$ nanoparticles. As shown in Example 8, the transparency of the microparticles can be adjusted in a systematic way by varying the $TiO_2$ nanoparticles concentration. This capability allows the cosmetic ingredient formulator wide latitude in the formulations of products when it is desired to adjust sensorial aspects for different kinds of sensorial benefits.

Accordingly, in embodiments of the microparticle of the invention, the $TiO_2$ nanoparticles are present at a concentration between about 0.2% w/w and about 25% w/w based on the weight of the CNC, depending on the desired effect (SPF boosting, whitening, etc.). Indeed, choosing a higher concentration of a pigment with SPF boosting properties will generally increase the SPF boosting properties of the resulting microparticle. For SPF boosting, the $TiO_2$ nanoparticles is preferably between 5 w/w % and 20% w/w, based on the weight of the CNC.

In preferred embodiments, the $TiO_2$ nanoparticles have a particle size between about 10 nm and about 500 nm.

Black Magnetite Nanoparticles

In other preferred embodiments, the inorganic pigment nanoparticles are black magnetite ($Fe_3O_4$) nanoparticles such as those sold by Sigma-Aldrich.

As mentioned, it has been found that using $Fe_3O_4$ particles of 1 micron in size may not allow for the producing of an effective pigment (see Comparative Example 7 discussed below). Accordingly, when $Fe_3O_4$ is used as the pigment nanoparticle, the $Fe_3O_4$ nanoparticles should preferably have a particle size of about 10 nm to about 500 nm. The preferred particle size of the magnetite nanoparticles is about 50 nm to about 100 nm (by SEM) with a preferred surface area of greater than 60 $m^2/g$ (as measured by the BET method).

Surprisingly, using $Fe_3O_4$ as a pigment will lead to a microparticle with a "skin colored" hue. Indeed, as shown in Examples 1 to 3, it has been found that black magnetite ($Fe_3O_4$) nanoparticles can bind to CNC microparticles. The resulting free-flowing powders exhibited brown hues, which depended on the concentration of $Fe_3O_4$ nanoparticles in the microparticles.

The higher the concentration of the $Fe_3O_4$, the darker the skin tone. Thus, in embodiments, the $Fe_3O_4$ nanoparticles can be present in the microparticles at a concentration from about 0.1% w/w to about 50% w/w, based on the combined weight of the cellulose nanocrystals and the $Fe_3O_4$ nanoparticles.

Ultramarine Nanoparticles

In yet another preferred embodiment of the present invention, the inorganic pigment nanoparticles are ultramarine nanoparticles. Ultramarine is a naturally occurring blue inorganic pigment that is also available as a synthetic pigment. It can be used to "cool" the color of a warm pigment, for example when formulated into a coloring medium like a makeup foundation. Examples 5 and 6 shows microparticles of the invention containing ultramarine nanoparticles.

Changing the concentration of the ultramarine nanoparticles in the microparticle will change its hue.

Bonding Between the Pigment Nanoparticles and the CNC

As mentioned above, bonding between the pigment nanoparticles and the CNCs can be covalent or noncovalent based on hydrogen bonding, ionic bonding, van der Waals interactions, hydrophobic interactions, or combinations of noncovalent interactions. In preferable embodiments, the bonding is noncovalent.

Bonding between pigment nanoparticles, e.g. comprising metal oxide, and the CNCs may involve chelation and/or bridging between CNC surface carboxylate anions, phosphate groups, or sulfate groups and the pigment nanoparticles, e.g. with metal cations. For example, the carboxylic acid group (—COOH), the nitro-dihydroxyphenylalanine group (—OH), the dihydroxyphenylalanine group, the phosphate group (—O—PO(OH)$_2$), and the amine group (—NH$_2$) can chelate to the surface of iron oxide nanoparticles. Carboxyl and sulfate groups also bind to titanium dioxide.

Furthermore, noncovalent bonding may involve hydrogen bonded interactions with surface hydroxyl groups of the pigment nanoparticles and surface hydroxyl groups and/or carboxylic acid or carboxylate groups of the CNCs.

Noncovalent bonding can also involve electrostatic interaction between charged pigment nanoparticles (e.g. metal oxide particles or organic pigment particles) and surface charge on the CNCs. In preferred embodiments, metal oxides pigment nanoparticles interact by hydrogen bonding with the CNC host, as shown in Example 9 (see below).

Binding of pigment nanoparticles (such as a metal oxide) to CNC can reduce the crystallinity index of the nanocrystal, expressed as percent crystallinity. This is especially the case when ultrasound is used to disperse and distribute the metal oxide.

Hue of the Microparticles of the Invention

The hue of the microparticles can be adjusted to appear cool or warm depending on the type of dye(s) or pigment(s) combined with the dominant color provided by the pigment nanoparticles. Thus, a cool green can be warmed by adding traces of a warm yellow. A cool red can be warmed by adding traces of yellow or orange.

As discussed above and shown in the Examples below, skin-tone pigments offer the ability to prepare a vast range of skin tones using only $Fe_3O_4$ nanoparticles combined at various ratios with CNC. As mentioned, the higher the concentration of $Fe_3O_4$ nanoparticles, the darker the skin tone.

In addition, as also discussed above and shown in the Examples below, the skin tone can be adjusted to be warmer or cooler by adding other pigments, inorganic or organic. This is advantageous because it removes the need to add other iron oxides such as red and yellow, as these have a limited color range.

Method of Producing Microparticles Comprised of CNCs with Pigment Nanoparticles Bound Thereto In a second aspect of the invention, a method for producing the above microparticles is provided.

The method for producing the microparticles thus comprises the steps of:
a. producing an aqueous suspension of carboxylated, sulfated, or phosphated CNCs with pigment nanoparticles bound thereto; and
b. drying said aqueous suspension to produce the microparticles,
  wherein the pigment nanoparticles are nanoscale particles of at least one organic pigment, at least one inorganic pigment, or both.

Starting Material

The starting material can be any of the carboxylated, sulfated, or phosphated CNCs defined in the previous section, as well as the pigment nanoparticles defined in the previous section. It is generally understood that the wt % of the pigment nanoparticles present in the aqueous suspension (when compared to the CNCs) will generally reflect the wt % of the pigment nanoparticles in the resulting microparticles. As mentioned above, the wt % of the pigment nanoparticles in the microparticles refers to the weight of the pigment nanoparticles in comparison to the combined weight of the pigment nanoparticles and the CNCs.

In embodiments, the carboxylated, sulfated, or phosphated CNCs are produced by carboxylating, sulfating, or phosphating CNCs, which can be done using any known method in the art.

Suspension Step a)

In this step, an aqueous suspension comprising the above starting ingredients is produced. This is generally accomplished by first producing an aqueous suspension of carboxylated, sulfated, or phosphated CNCs and then adding the pigment nanoparticles thereto. The starting ingredients are then mixed together to produce the aqueous suspension with the pigment nanoparticles bound to the CNCs.

The mixing of the starting ingredients can be done using any known method in the art, provided that the starting ingredients are sufficiently mixed. In embodiments, the starting ingredients are stirred (preferably using a magnetic stirrer) and/or sonicated; the mixing should be performed for sufficient time to bind the pigment nanoparticles to the CNCs.

In preferred embodiments, the starting materials are vigorously stirred using a magnetic stirrer and simultaneously sonicated (Sonics Vibra Cell) for 20 minutes at 80% amplitude (using a probe sonicator).

Optionally, dyed cellulose nanocrystals (produced as described in WO 2017/091893) of at least one hue may be added to the suspension before and/or after the mixing of the suspension.

Drying Step b)

In this step, the aqueous suspension comprising the starting ingredients is dried in order to produce the microparticles of the present invention.

The drying of the aqueous suspension can be performed using any known method in the art that will produce microparticles with the dimensions defined in the previous section. In preferred embodiments, the aqueous suspension is oven dried or spray dried, more preferably spray-dried. In even more preferred embodiments, the aqueous suspension is spray dried with a Buchi spray dryer (inlet temperature 175° C., pump speed 30%, aspirator 70%, air pressure 600 NL/h).

Advantages of the Invention

In developing the microparticle of the present invention, the inventors discovered the surprising result that inorganic or organic pigments will bind to cellulose nanocrystals. This is even more surprising because the pigment nanoparticles are on the same order of size, or larger, than the CNC crystallites.

In addition to the advantages previously discussed, the microparticles of the present invention can present one or more of the following advantages:
  The microparticles exhibit a soft feel that is superior to the feel of conventional pigments. Skin feel is an extremely important property of e.g., cosmetic preparations. Preparations with good, or preferably excellent, skin feel are preferred by customers;
  The microparticles allow for wide latitude in the formulation of products when it is desired to adjust sensorial aspects for different kinds of sensorial benefits (for example, transparency of the microparticles can be adjusted in a simple and systematic way);
  Allows for the binding of pigment nanoparticles to cellulose nanocrystals without the use of a polyelectrolyte (in contrast to the pigments of WO 2017/091893);
  The crystalline nanocellulose comprises most of the content of the hybrid pigments, yet the resulting pigments yield colors (red and blue for example) that are very vibrant to the eye.
  The microparticles have an augmented naturality index, being composed predominantly of cellulose, meaning the microparticles can be derived in whole or in part from natural sources.
  The microparticles of the present invention allow the creation of new kinds of pigments that have potential to lie almost anywhere within the CIE color space. This capability expands the gamut of colors that can be obtained by the method of producing said microparticles. The capability arises because the color mixing to obtain new hues occurs at the nanoscale and in some cases can be combined with color formation at the molecular scale. For instance, one can envisage combining an ultramarine nano-pigment with molecular dye FD&C yellow 5 to make a green pigment. It follows that, in embodiments of the microparticle of the present invention, many skin tone pigments can be made. In fact, the large possible color gamut obtainable with the microparticles of the present invention is necessary to match both the subtle and broad variations among skin tones.
  The microparticles of the present invention do not have to be milled to exhibit desirable sensorial aspects like smooth and silky feel.
  The method of the present invention produces the above-defined microparticles. In addition, in embodiments, the method of the present invention is relatively simple and can be easily adjusted to produce a wide variety of microparticles.

Moreover, in embodiments, the method of the present invention allows for better reproducibility of pigment hues. Typically, to ensure reproducibility of a hue, researchers often make measures of the L*a*b (Lab color) parameters. L* represents the lightness and a* and b* represent the green-red and blue-yellow color components within the so-called CIELAB color space. Lab color is designed to approximate human vision. Obtaining batch to batch uniformity is important when blending pigment powders. One method of measuring uniformity is to determine the global color difference delta E, as defined by the standard CIEDE (2000).

However, with conventional pigments, it can be difficult to ensure batch to batch uniformity. Conversely, in embodiments, the method of the present invention does not require the physical mixing of powder pigments; accordingly, reproducibility is more easily achieved. In addition, in embodiments, the method of the present invention takes advantage of the synergies between FDA certified organic colorants and inorganic colorants.

Furthermore, in embodiments of the method of the present invention, fewer steps are required after production of the pigment, while offering similar benefits to conventional methods that have more steps (such as surface treatment or coating).

Applications in Cosmetic Preparations

The microparticles of the invention can be used in a cosmetic preparation. For example, they can replace or be used concurrently with pigments currently used in such preparations. Thus, in another aspect of the invention, there is provided a cosmetic preparation comprising the above microparticles and one or more cosmetically acceptable ingredients.

The nature of these cosmetically acceptable ingredients in the cosmetic preparation is not crucial. Ingredients and formulations well-known to the skilled person may be used to produce the cosmetic preparation.

Herein, a "cosmetic preparation" is a product intended to be rubbed, poured, sprinkled, or sprayed on, introduced into, or otherwise applied to the human body for cleansing, beautifying, promoting attractiveness, or altering appearance. Cosmetics include, but are not limited to, products that can be applied to:

- the face, such as skin-care creams and lotions, cleansers, toners, masks, exfoliants, moisturizers, primers, lipsticks, lip glosses, lip liners, lip plumpers, lip balms, lip stains, lip conditioners, lip primers, lip boosters, lip butters, towelettes, concealers, foundations, face powders, blushes, contour powders or creams, highlight powders or creams, bronzers, mascaras, eye shadows, eye liners, eyebrow pencils, creams, waxes, gels, or powders, setting sprays;
- the body, such as perfumes and colognes, skin cleansers, moisturizers, deodorants, lotions, powders, baby products, bath oils, bubble baths, bath salts, body lotions, and body butters;
- the hands/nails, such as fingernail and toe nail polish, and hand sanitizer; and
- the hair, such as shampoo and conditioner, permanent chemicals, hair colors, hairstyling products (e.g. hair sprays and gels).

A cosmetic may be a decorative product (i.e. makeup), a personal care product, or both simultaneously. Indeed, cosmetics are informally divided into:

- "makeup" products, which are primarily products containing color pigments that are intended to alter the user's appearance, and
- "personal care" products encompass the remaining products, which are primarily products that support skin/body/hair/hand/nails integrity, enhance their appearance or attractiveness, and/or relieve some conditions that affect these body parts.

Both types of cosmetics are encompassed within the present invention.

A subset of cosmetics includes cosmetics (mostly personal care products) that are also considered "drugs" because they are intended for use in the diagnosis, cure, mitigation, treatment, or prevention of disease or intended to affect the structure or any function of the body of man or other animals. Examples include antidandruff shampoo, deodorants that are also antiperspirants, products such as moisturizers and makeup marketed with sun-protection claims or anti-acne claims. This subset of cosmetics is also encompassed within the present invention.

Definitions

The use of the terms "a" and "an" and "the" and similar referents in the context of describing the invention (especially in the context of the following claims) are to be construed to cover both the singular and the plural, unless otherwise indicated herein or clearly contradicted by context.

The terms "comprising", "having", "including", and "containing" are to be construed as open-ended terms (i.e., meaning "including, but not limited to") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein. All subsets of values within the ranges are also incorporated into the specification as if they were individually recited herein.

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise claimed.

No language in the specification should be construed as indicating any non-claimed element as essential to the practice of the invention.

Herein, the term "about" has its ordinary meaning. In embodiments, it may mean plus or minus 10% or plus or minus 5% of the numerical value qualified.

Unless otherwise defined, all technical and scientific terms used herein have the same meaning as commonly understood by one of ordinary skill in the art to which this invention belongs.

Other objects, advantages and features of the present invention will become more apparent upon reading of the following non-restrictive description of specific embodiments thereof, given by way of example only with reference to the accompanying drawings.

DESCRIPTION OF ILLUSTRATIVE EMBODIMENT

The present invention is illustrated in further details by the following non-limiting examples.

CNC Stock Suspension No. 1

Each of the following Examples used a CNC stock suspension prepared according to the following method, unless indicated otherwise. A sodium carboxylate salt of nanocrystalline cellulose (cCNC) was produced as described in International patent publication no. WO 2016\015148 A1. Briefly, dissolving pulp (Temalfa 93) is suspended in 30% aqueous hydrogen peroxide and heated to reflux with vigorous stirring over a period of 8 hours. The resulting dispersion is diluted with water, purified by diafiltration and then neutralized with aqueous sodium hydroxide. The resulting CNC carboxylate was prepared to a concentration of 3.56% w/v.

Example 1: 13.5% $Fe_3O_4$ in CNC Brown Pigment 28 mL of stock CNC suspension no. 1 were added to a 100 ml beaker. The suspension was stirred rapidly (magnetic stirrer). To the stirred CNC suspension were added 156 mg of Fe3O4 (Sigma Aldrich, Iron (II, III) Oxide, <50 μm). The suspension was vigorously stirred (magnetic stirrer) and simultaneously sonicated (Sonics® Vibra-Cell®) for 20 minutes at 80% amplitude (probe sonicator). The well-mixed suspension was spray dried with a Buchi® spray dryer (inlet temperature 175° C., pump speed 30%, aspirator 70%, air pressure 600 NL/h) to yield a free-flowing dark brown powder. Mean CNC/$Fe_3O_4$ pigment microparticle size was 5 μm.

Figure 1B:
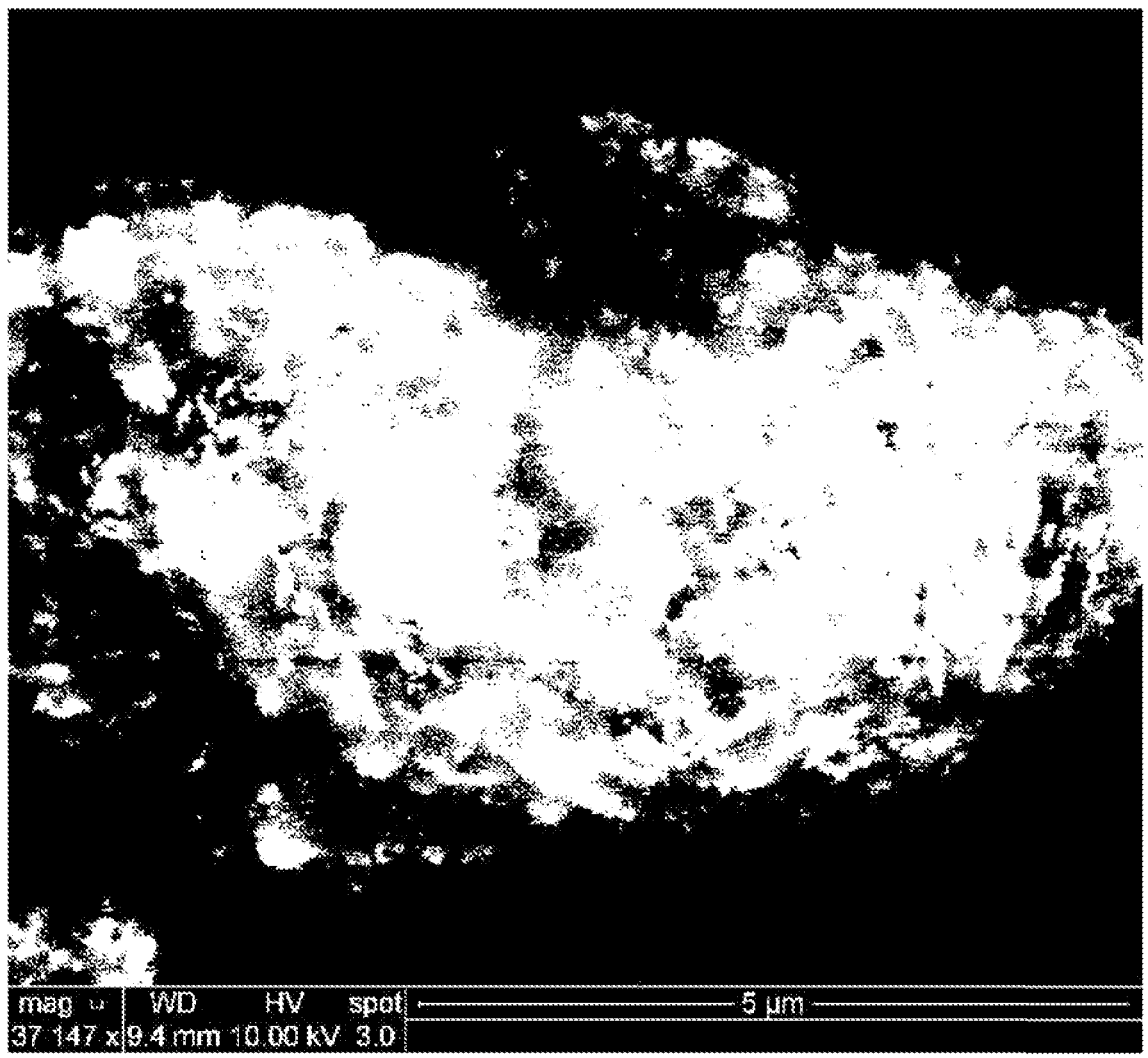

FIGS. 1a and 1b are SEM images of the microparticles obtained. Iron oxide nanoparticles, which are observed as small light protrusions on the surface of a near spherical microparticle in FIG. 1a, are bound to CNC microparticles. Element-specific imaging shown in FIG. 1b by SEM confirms the presence of iron-containing nanoparticles as bright areas on the surface of the composite iron oxide/CNC pigment microparticles. FIGS. 1(a) and 1(b) also show 2 different particle shapes—one spherical and one globular—that emerge when 13.5% $Fe_3O_4$ is spray dried with CNC to make microspheres.

Figure 2A:
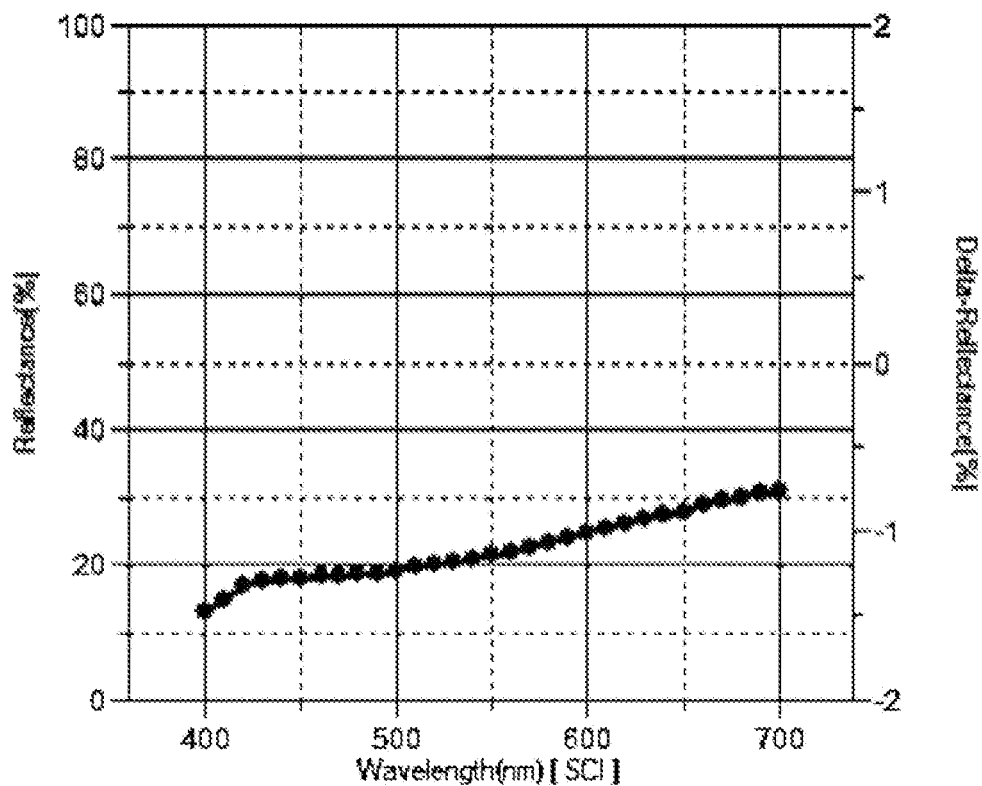
FIG. 2a shows the reflectance spectrum of the microparticles of Example 1: 13.5% $Fe_3O_4$ in CNC.
Figure 2B:
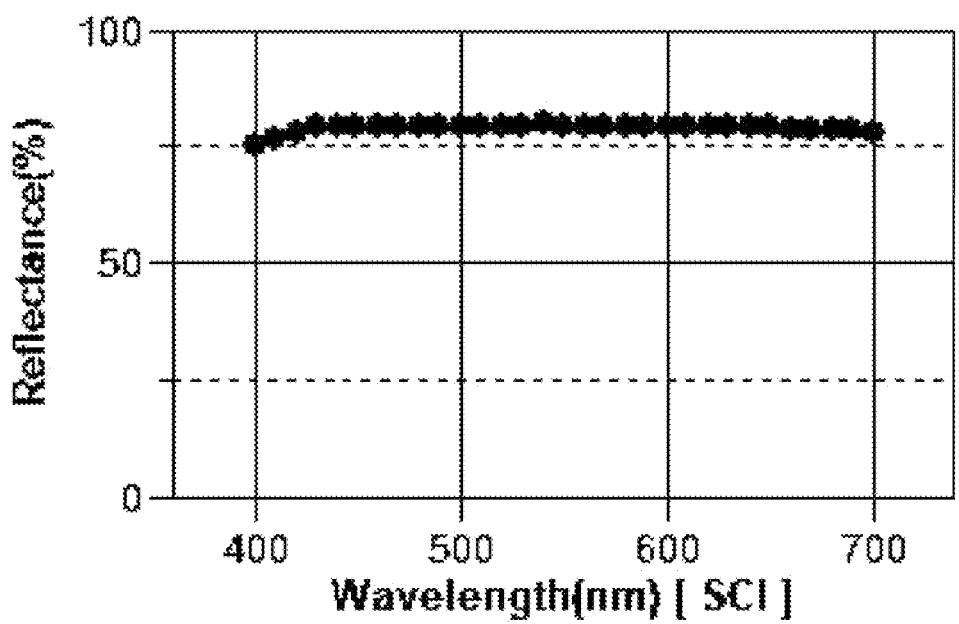
FIG. 2b shows the reflectance of CNC microparticles with no added iron oxide.

The microparticles exhibited a brown hue. FIG. 2a shows the reflectance spectrum of the microparticles. The pigment powder exhibits low reflectance in the range 400-700 nm. FIG. 2b shows the reflectance of CNC microparticles with no added iron oxide.

Example 2: Approximately 5% $Fe_3O_4$ in CNC Pigment 28 mL of stock CNC suspension no. 1 were added to a 100 ml beaker. The suspension was stirred rapidly (magnetic stirrer). To the stirred CNC suspension were added 53 mg of $Fe_3O_4$ (Sigma Aldrich, Iron (II, III) Oxide, <50 μm). The suspension was vigorously stirred (magnetic stirrer) and simultaneously sonicated (Sonics® Vibra-Cell®) for 20 minutes at 80% amplitude (probe sonicator). The well-mixed suspension was spray dried with a Buchi® spray dryer (inlet temperature 175° C., pump speed 30%, aspirator 70%, air pressure 600 NL/h) to yield a free-flowing medium brown powder. Mean particle size was 5 μm.

Figure 3:
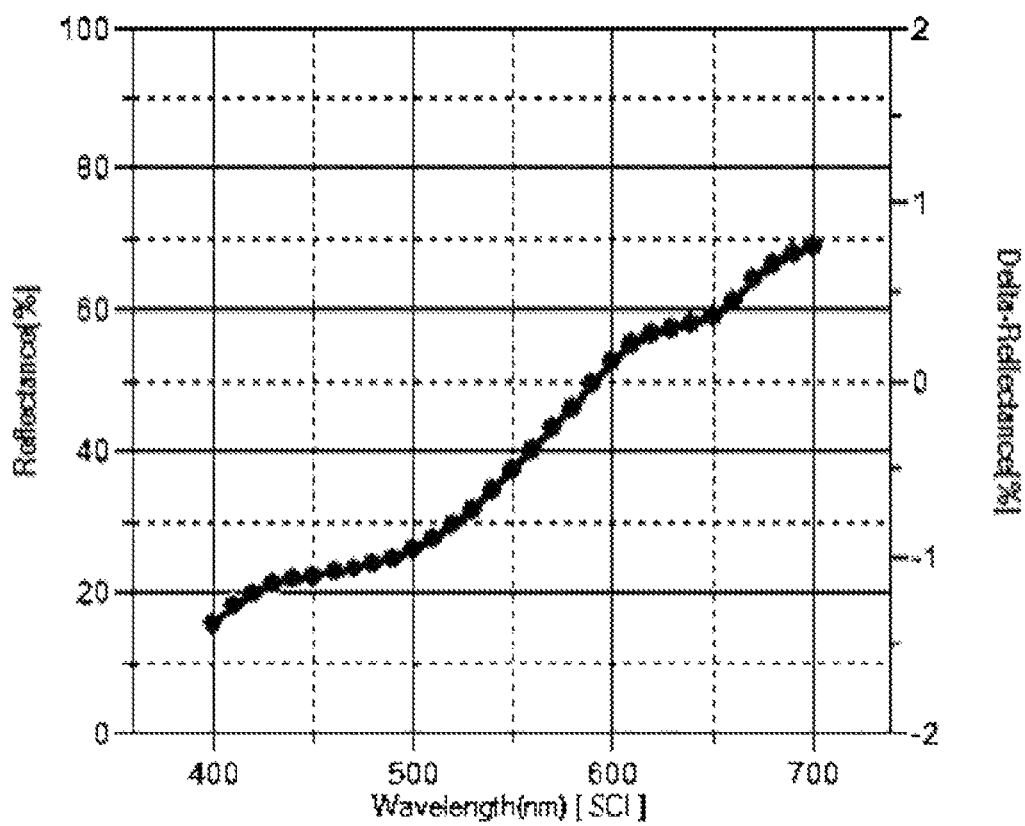
FIG. 3 shows the reflectance spectrum of the microparticles of Example 2: 5% $Fe_2O_3$ in CNC.

FIG. 3 shows the reflectance spectrum of the microparticles. The microparticles had a brown hue that differed from the sample containing 13.5% Fe3O4 (Example 1). This is evident by comparing the reflectance spectra of FIGS. 2 (Example 1) and 3.

Example 3: Light Neutral Skin Tone Pigment—1% $Fe_3O_4$ CNC Pigment 28 mL of stock CNC suspension no. 1 were added to a 100 ml beaker. The suspension was stirred rapidly (magnetic stirrer). To the stirred CNC suspension were added 5 mg of $Fe_3O_4$ (Sigma Aldrich, Iron (II, III) Oxide, <50 μm). The suspension was vigorously stirred (magnetic stirrer) and simultaneously sonicated (Sonics® Vibra-Cell®) for 20 minutes at 80% amplitude (probe sonicator). The well-mixed suspension was spray dried with a Buchi® spray dryer (inlet temperature 175° C., pump speed 30%, aspirator 70%, air pressure 600 NL/h) to yield a free-flowing light brown powder.

The microparticles had a light neutral skin tone.

Example 4: Warm Neutral Skin Tone Pigment—1% $Fe_3O_{4+0.5}$% Red-40 CNC

This Example demonstrates how a warm, neutral skin tone can be obtained by combining an aqueous suspension of red 40 dye-CNC microparticles with an aqueous suspension of magnetite nanoparticles and CNC.

Red-40 Dye-CNC Microparticles

To make the red 40 dye-CNC microparticles, first, a carboxylated CNC suspension was prepared as follows: a solution of 30% $H_2O_2$ in water (2.5 L) was heated to reflux. 200 g of Temalfa 93™ (~1 cm×5 cm strips) were added to the boiling $H_2O_2$ solution. This mixture was stirred vigorously for 8 hours. The reaction produced a white suspension of carboxylated CNC (cCNC). The reaction was stopped by adding ice to dilute the suspension to 4 L. The carboxylated CNC was purified by diafiltration using a 10 kDa hollow fiber filter from Spectrum Labs. Once the conductivity of the permeate was below 100 μS/cm, the cCNC solution was neutralized with NaOH and sonicated for 5-20 mins at 80-100% output using a Sonics Vibra-cell VCX130. Diafiltration was again used until the conductivity of the permeate reached <20 μS/cm. The suspension was then concentrated and collected.

A portion of this cCNC was than combined with a cationic polyelectrolyte to invert the potential of the cCNC. Thus, a 1 L suspension of the above cCNC in water (0.5% w/v, 5 g) was equipped with a stir bar and a SONICS VIBRA-CELL VCX130 probe sonicator. The suspension was stirred and sonicated at 100% output for 10 minutes. Immediately following this, 20 mL of a solution of polyquaternium salt in the form of poly(diallyldimethylammonium chloride) (PDDA, also called polyquaternium-6, <100 kDa molecular weight) in water (3.5% w/v, 0.7 g) was rapidly added to the cCNC. Sonication was continued for 40 min to yield a stable viscous suspension. This product was purified by diafiltration using a 10 kDa MW cut-off filter until conductivity of the permeate was <20 μS/cm. A stable translucent suspension of positively charged CNC particles (CNC+) resulted.

The red 40 dye-CNC pigment was made as follows: a beaker containing 1 L of the above CNC+(0.5% w/v, 5 g) was fixed under a Rayneri mixer. The CNC+ suspension was rapidly mixed while slowly adding a 100 mL solution of (FD&C Red 40, Allura Red AC, E129) dye dissolved in water (0.5% w/v, 0.5 g). Stirring was continued for an additional 20 minutes. The sample was spray dried with a Techni Process model SD 3.5 Pilot Plant spray dryer (inlet temperature 175° C., outlet temperature 68° C., air pressure was set at 50 psi, approximately 10 L/h of feed flow to the dryer).

Microparticles with $Fe_3O_4$ Pigments 28 mL of stock CNC suspension no. 1 was added to a 50 mL beaker. To the stirred CNC suspension were added 10 mg of $Fe_3O_4$ (1%) and 5 mg of the above red 40 dye-CNC pigment (0.5%) prepared as described above. This suspension was stirred and sonicated for 30 minutes at 80% amplitude, breaking up the red 40 dye-CNC microparticles into its constituting nanocrystals (or chunks thereof). The well-mixed suspension was spray dried with a Buchi® spray dryer (inlet temperature 175° C., pump speed 30%, aspirator 70%, air pressure 600 NL/h) to yield a free-flowing warm light beige powder. The mean particle size was 5 μm.

Figure 4:
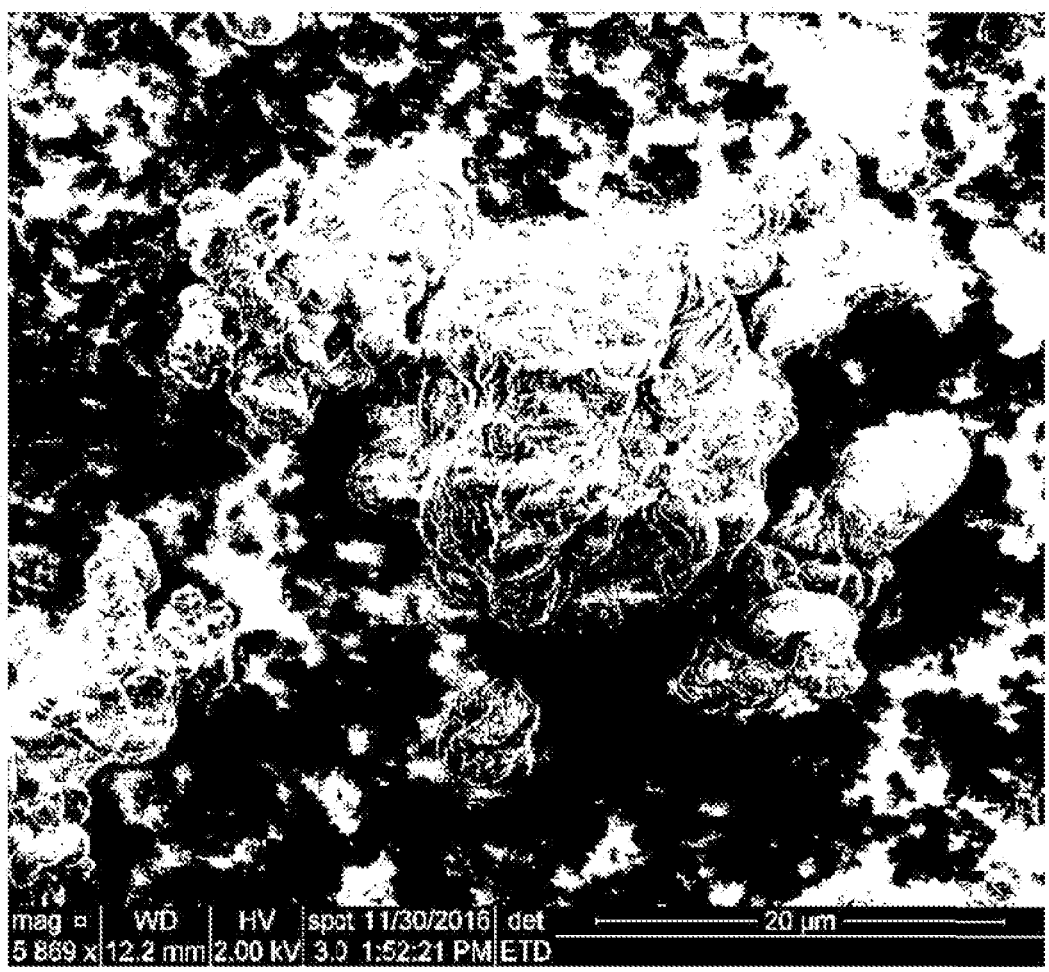
FIG. 4 is an SEM image of the microparticles of Example 4: 1% $Fe_3O_4$+0.5% Red 40-CNC$^+$ in CNC.

FIG. 4 is an SEM image of the microparticles obtained. Element-specific imaging by SEM reveals the presence of iron-containing nanoparticles on the surface of the microparticles. In addition, FIG. 4 shows that rough globular particles are produced when 1% $Fe_3O_4$ and 0.5% Red 40 are spray dried to make CNC microspheres.

Figure 5:
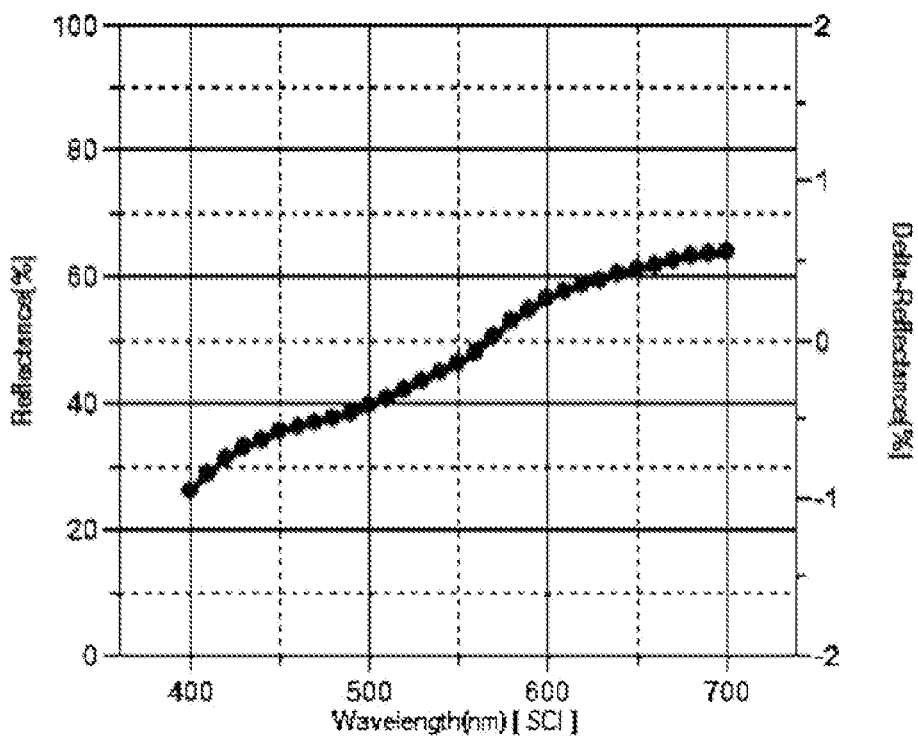
FIG. 5 shows the reflectance spectrum of the microparticles of Example 4: 1% $Fe_3O_4$+0.5% Red 40-CNC$^+$ in CNC.

FIG. 5 shows the reflectance spectrum of the microparticles.

Example 5: 5% Ultramarine Blue CNC Pigment 28 mL of stock CNC suspension no. 1 was added to a 100 ml beaker. The suspension was stirred rapidly. 25 mg of ultramarine blue pigment (SunCroma Ultramarine Blue; Product Code: C431810—Sun Chemical approximate size 1 μm) was added with vigorous stirring (magnetic stirrer) and simultaneously sonicated (Sonics® Vibra-Cell®) for 20 minutes at 80% amplitude (probe sonicator). The well-mixed suspension was spray dried with a Buchi® spray dryer (inlet temperature 175° C., pump speed 30%, aspirator 70%, air pressure 600 NL/h) to yield a free-flowing vibrant light blue powder. Mean particle size was 5 μm.

Material losses due to spray drying yield a loading of approximately 5% ultramarine in the obtained hybrid microsphere pigment.

Figure 6:
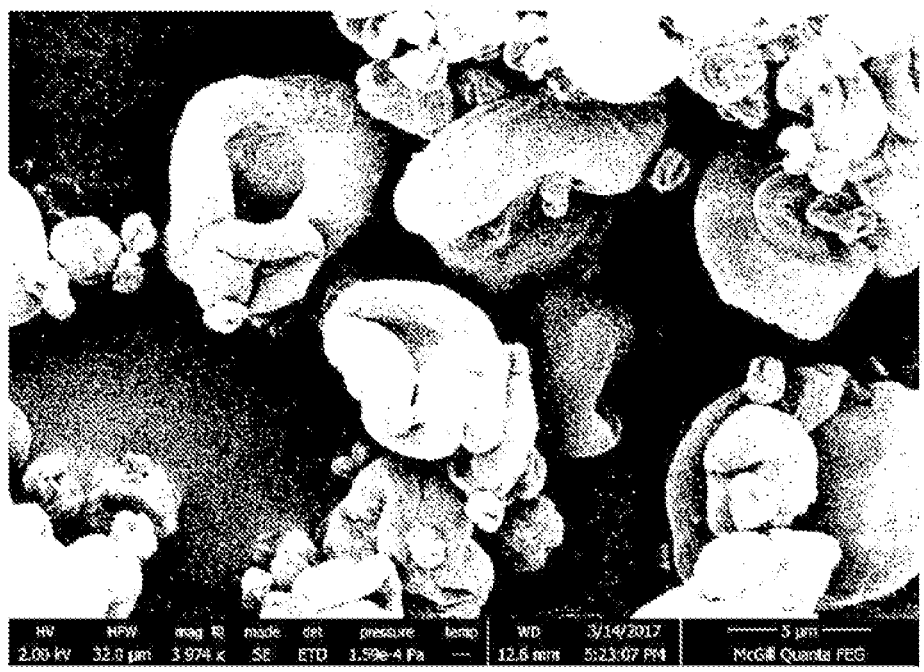
FIG. 6 is an SEM image of the microparticles of Example 5: 5% Ultramarine Blue in CNC.

FIG. 6 is an SEM image of the microparticles of obtained. FIG. 6 shows that the resulting micron-scale pigment particles are irregularly shaped objects.

Figure 7:
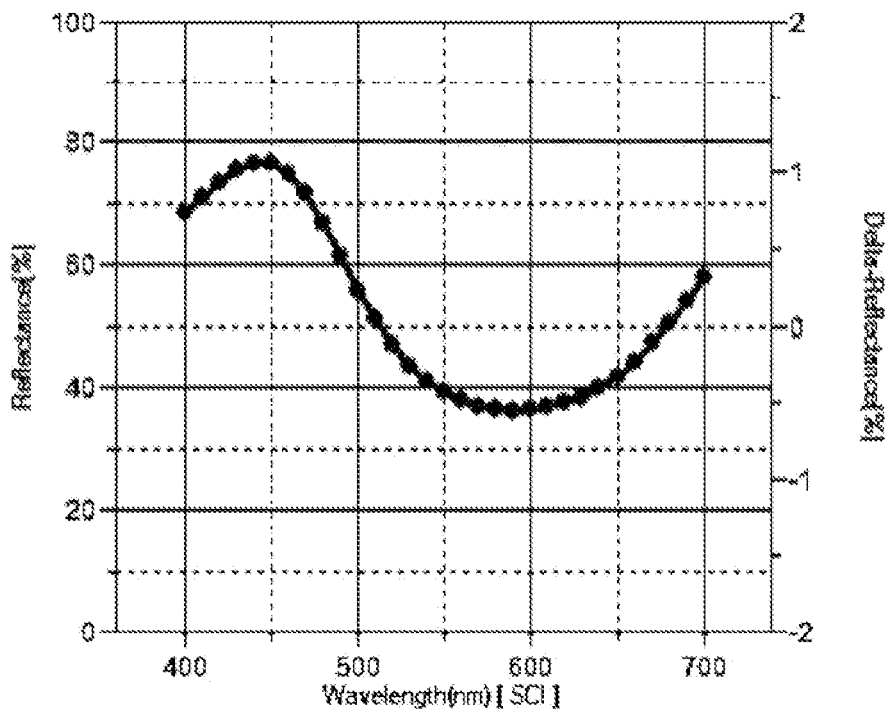
FIG. 7 shows the reflectance spectrum of the microparticles of Example 5: 5% Ultramarine Blue in CNC.

FIG. 7 shows the reflectance spectrum of the microparticles.

The powder so produced is experienced as providing a soft feel to the touch.

Example 6: 50% Ultramarine Blue CNC Pigment 14 mL of stock CNC suspension no. 1 was added to a 100 ml beaker. The suspension was stirred rapidly. 500 mg of ultramarine blue pigment (SunCroma Ultramarine Blue; Product Code: C431810—Sun Chemical, approx. size 1 um) was added with vigorous stirring (magnetic stirrer) and simultaneously sonicated (Sonics® Vibra-Cell®) for 20 minutes at 80% amplitude (probe sonicator). An additional 5 mL of water was added to with further mixing to dilute the mixture before spray drying. The well-mixed suspension was spray dried with a Buchi® spray dryer (inlet temperature 175° C., pump speed 30%, aspirator 70%, air pressure 600 NL/h) to yield a free-flowing vibrant deep blue powder. Mean particle size is 5 μm.

Figure 8:
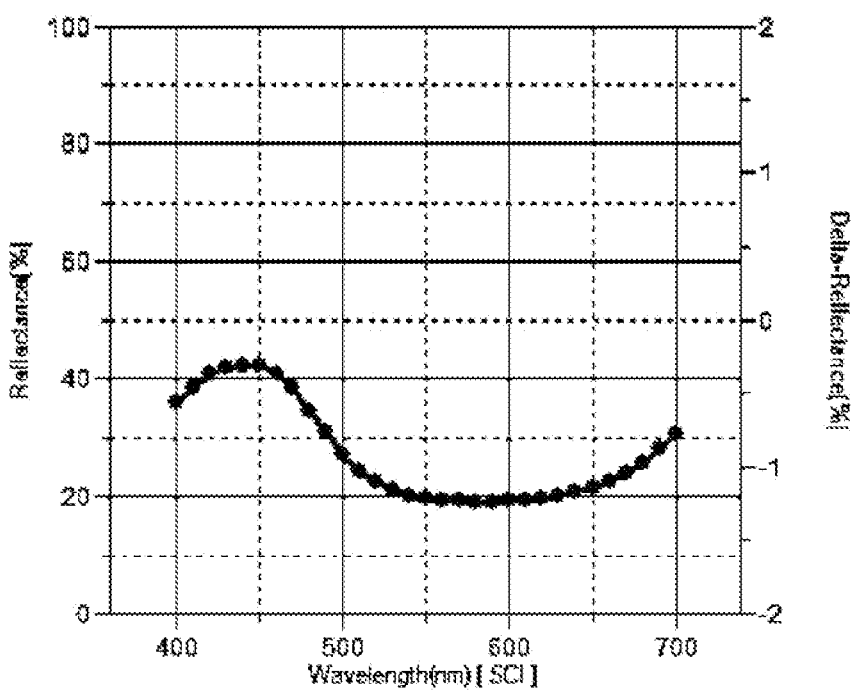
FIG. 8 shows the reflectance spectrum of the microparticles of Example 6: 50% Ultramarine Blue in CNC.

FIG. 8 shows the reflectance spectrum of the microparticles obtained.

Example 7: (Comparative) Micron-Size $Fe_3O_4$ Powder does not Yield a CNC Pigment 28 mL of stock CNC suspension no. 1 were added to a 100 ml beaker. The suspension was stirred rapidly. 25 mg of micron-size $Fe_3O_4$ (SunChroma black iron oxide—Product Code C335198—Sun Chemical; approx. size 1 μm) pigment were added with vigorous stirring (magnetic stirrer) and simultaneously sonicated (Sonics® Vibra-Cell®) for 20 minutes at 80% amplitude (probe sonicator). The grey suspension was spray dried with a Buchi® spray dryer (inlet temperature 175° C., pump speed 30%, aspirator 70%, air pressure 600 NL/h) to yield a gray powder. Mean particle size was 5 μm.

Figure 9:
FIG. 9 is an SEM image of the microparticles of Comparative Example 7: 5% micron-size black iron oxide in CNC.

FIG. 9 is an SEM image of the microparticles obtained. The powder contained visible evidence of magnetite microparticles. Accordingly, micron-size $Fe_3O_4$ did not allow for the producing of an effective pigment.

Figure 10:
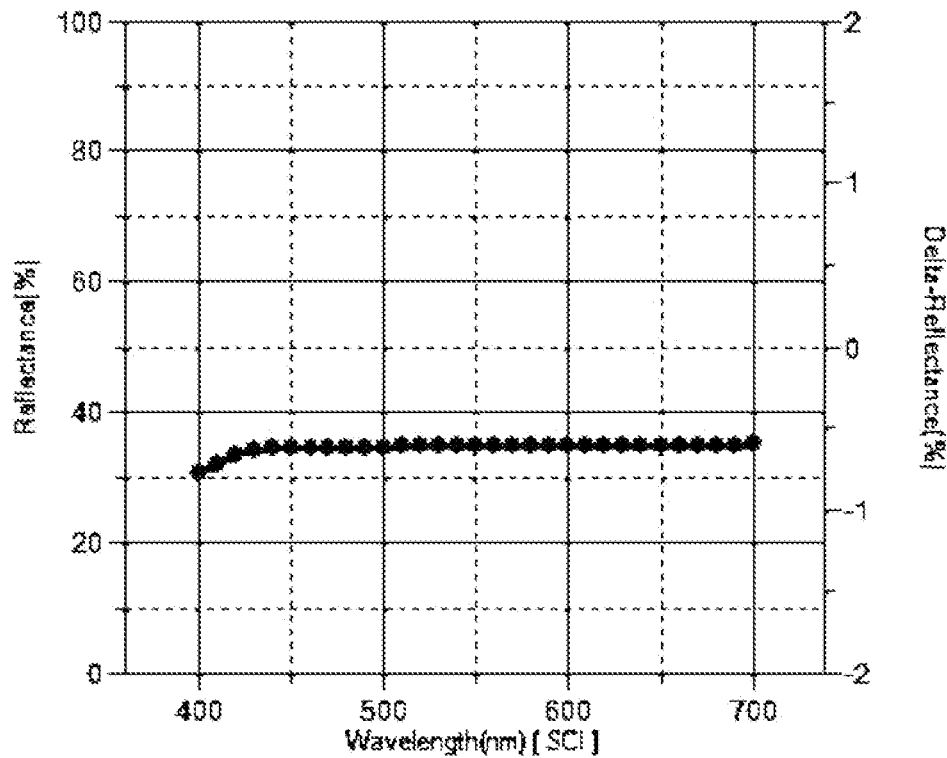
FIG. 10 shows the reflectance spectrum of the microparticles of Comparative Example 7: 5% micron-size black iron oxide in CNC.

FIG. 10 shows the reflectance spectrum of the microparticles.

Example 8: CNC Pigment with SPF Booster $TiO_2$

Aeroxide TiO2 P25 (available from Evonik® Industries), which was used for this Example, is a fine white, hydrophilic powder. It consists of aggregated primary particles. The aggregates are several hundred nm in size and the primary particles have a mean diameter of approx. 21 nm. The surface area as measured by BET is 50+/−15 m2/g. The weight ratio of anatase and rutile is approximately 80/20

34 mL of stock suspension no. 1 was diluted with 11 mL of deionized water to a final volume of 45 mL. To a 100 ml beaker containing 45 mL of a 2.7% w/v of CNC stock suspension no. 1, 0.405 g of Aeroxide P25 $TiO_2$ powder, was added with vigorous stirring (magnetic stirrer) and simultaneous sonication (Sonics® Vibra-Cell®) for 20 minutes at 80% amplitude (probe sonicator). This produced a 25 wt % $TiO_2$ slurry.

By adjusting how much $TiO_2$ was added, 1, 5, 10, 15, 20 and 25 wt % $TiO_2$ suspensions were also made using the same procedure as above.

In each case, the well-mixed suspension was spray dried with a Buchi® spray dryer (inlet temperature 175° C., pump speed 30%, aspirator 70%, air pressure 600 NL/h) to yield a free-flowing white powder.

Comparative cellulose microparticles were prepared similarly as above but did not contain any $TiO_2$.

The produced powder exhibited a soft feel that was superior to the feel of conventional pigments, like nano-titanium dioxide alone.

Figure 11A:
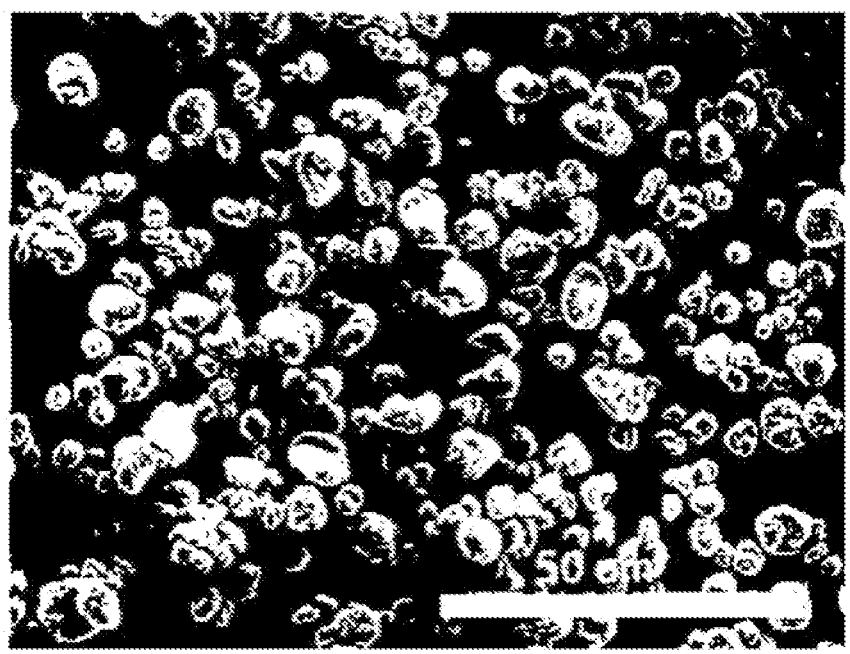
FIGS. 11a, 11b, and 11c are each an SEM image showing the microparticles of Example 8: 20% $TiO_2$ in CNC.
Figure 11B:
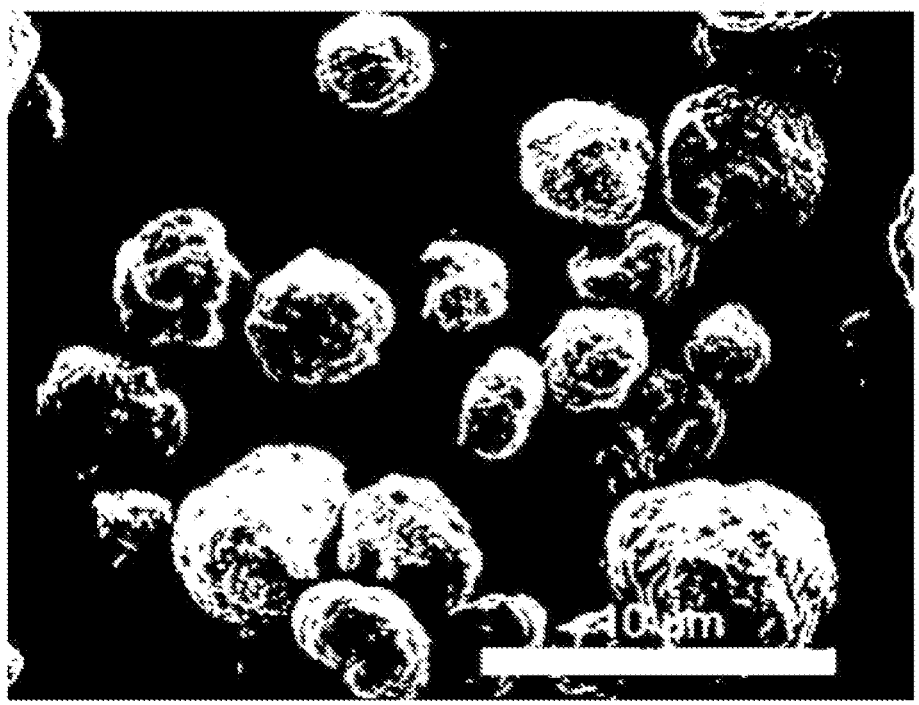
Figure 11C:
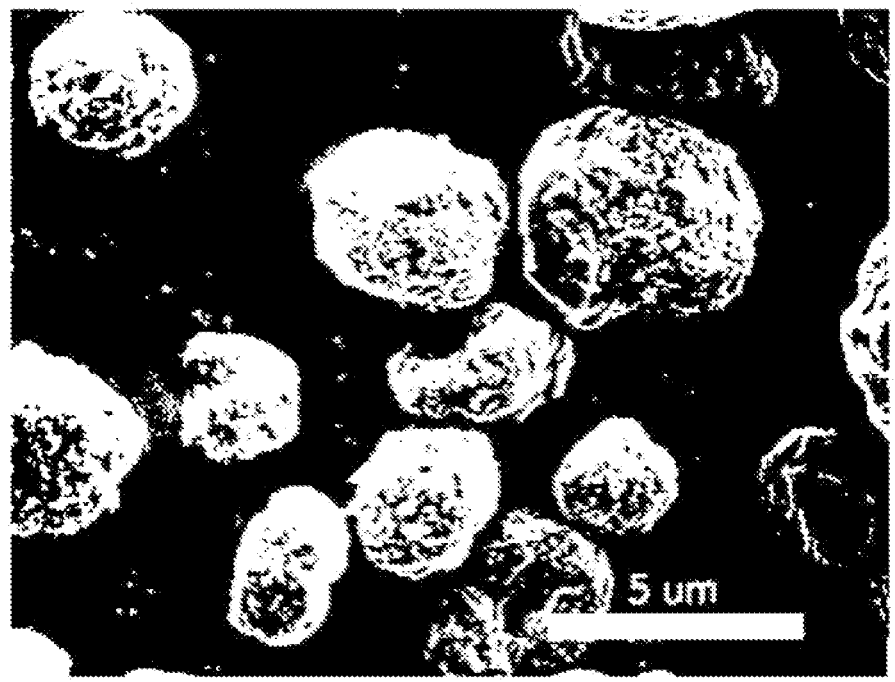

FIGS. 11a, 11b, and 11c are each an SEM image showing the microparticles containing 20% $TiO_2$ in CNC, under increasing magnification. These images show titanium dioxide nanoparticles bound to the surface, near subsurface, and most probably, to the interior of the microparticle.

Figure 12:
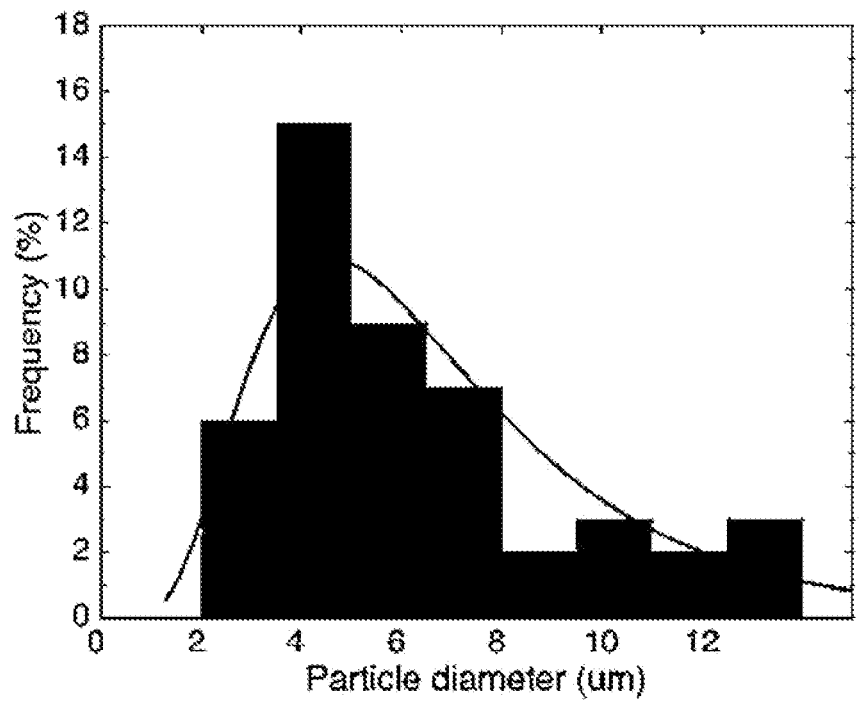
FIG. 12 shows the particle size distribution of the microparticle of Example 8: 20% $TiO_2$ in CNC.

FIG. 12 shows the particle size distribution of the microparticle containing 20% $TiO_2$ in CNC.

Particle morphology and $TiO_2$/CNC pigment size distributions were the same for 1, 5, 10, 15, and 25 wt % TiO2 compositions.

Transmittance of the Microparticles

Figure 13:
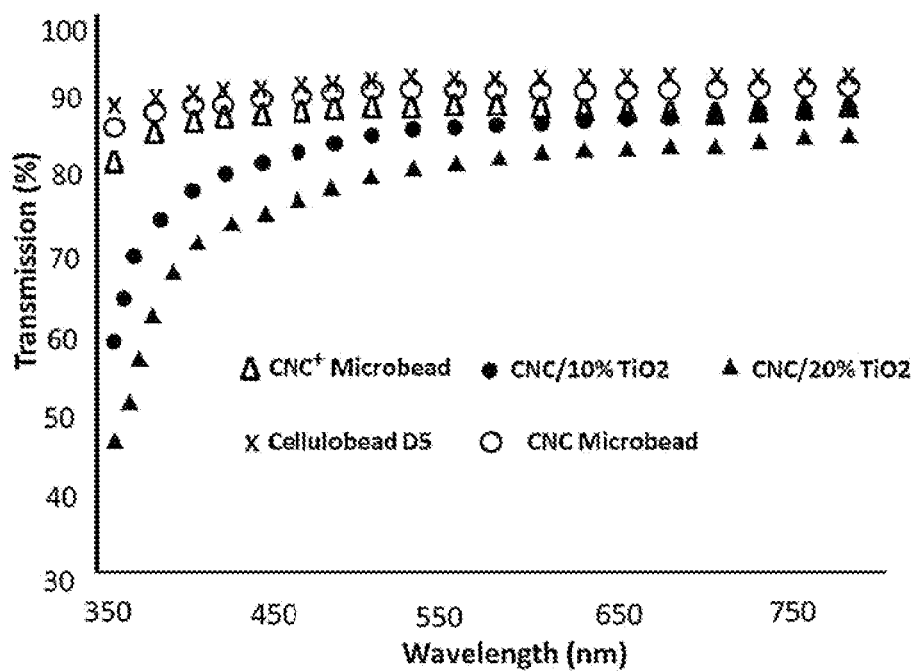
FIG. 13 is a graph showing the percentage of light transmitted by various microparticles, including certain microparticles from Example 8, formulated in dimethicone at a film thickness of 50 µm.

FIG. 13 compares the optical transmittance as a function of wavelength of various microparticles, including the 10% TiO2 microparticles and the 20% TiO2 microparticles defined above, hosted in dimethicone (Shin Etsu), a poly (dimethylsiloxane) fluid commonly used in cosmetic formulation. The curves were obtained by measuring the transmittance of 10% w/w loadings of microparticles in dimethicone fluid, coated by precision wire bar to a thickness of 50 μm on a fused silica substrate. The Figure compares the UV absorbing response of the various microparticles in the range 350 nm and beyond.

Cellulobead D5 is a nominally 5 μm commercial cellulose type II microbead offered by Daito Kasei. This microbead is manufactured by the viscose process, which accounts for the different crystalline phase compared with CNC microbeads, which are the naturally occurring type I cellulose.

CNC+ is a microbead manufactured as above, but that contains 10% PDDA.

The CNC microbead manufactured as above, but does not contain PDDA or $TiO_2$.

The presence of 10% and 20% nano-$TiO_2$ to the CNC microbead confers greater extinction (lower % transmission)

in the UV region, with the 20% composition providing highest extinction. The graph illustrates that the hybrid pigment particles with $TiO_2$ offer a boost in UV protection, as confirmed by the SPF study described below.

Figure 14:
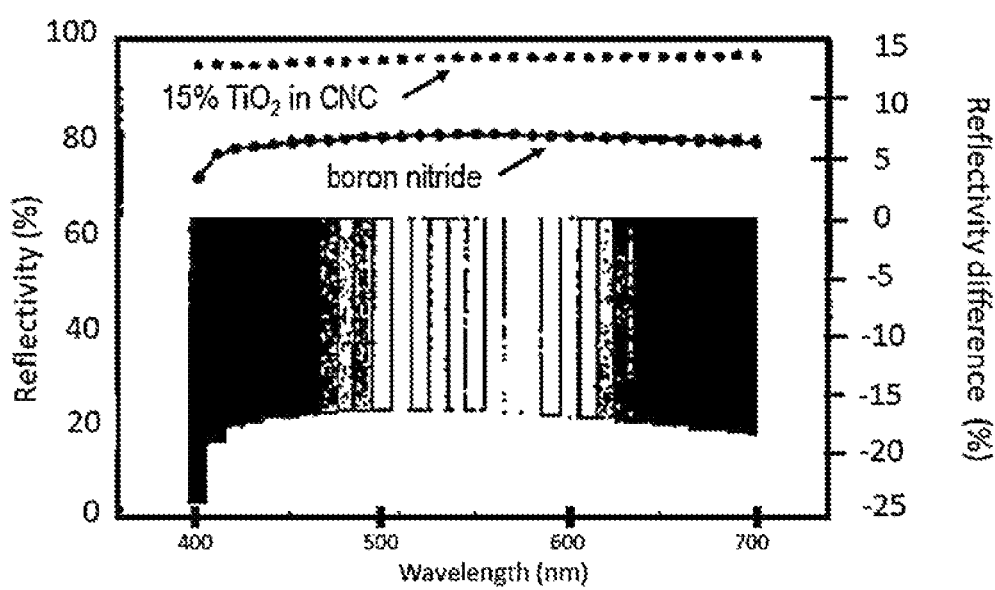
FIG. 14 shows the reflectance spectrum of the microparticles of Example 8: 15% $TiO_2$ in CNC (top curve) compared to that of boron nitride (bottom curve).

FIG. 14 shows the reflectance spectrum of the microparticle powder containing 15% $TiO_2$ in CNC obtained from the present Example (top curve) compared to that of boron nitride (St. Gobain Ceramics—Trade name, Boron Nitride UHP 1109C) (bottom curve).

SPF Testing

The purpose of the study of SPF was to determine the critical wavelength using an "in vitro" method based on the FDA final monograph 21 CFR 20'1.327(j). published on Jun. 17, 2011. The critical wavelength is identified as the wavelength at which the integral of the spectral absorbance curve reaches 90% of the integral over the UV spectrum from 290 to 400 nm. It has been settled that this value must be equal to or higher than 370 nm so as to classify the product as "broad spectrum".

The in vitro sun protection factor (SPF) after irradiation was provided following the same method. A comparative assay was made of non-treated plates against plates treated with a test product. This was based on the evaluation of UV transmittance through a thin film of sunscreen sample spread on a roughened substrate before and after exposure to a controlled dose of UV radiation from a defined UV source. A "Kontron 933" spectrophotometer equipped with an UV source, an integrating sphere and a monochromatic light source able to deliver a flow of energy between 290 and 400 nanometers was used. The transmittance values were measured at 1 nanometer intervals. A precision laboratory balance ($10^{-4}$ g) was used to control deposited product weight. Irradiation was provided by a Suntest Atlas CPS+ unit with a standard filter. Temperature regulation of the equipment in the range 25-35° C. was done. A pre-irradiation dose of 4 times 200 j/m2-eff (800 j/M2-eff) was delivered.

The substrate was the material to which the sunscreen product was applied. Polymethylmethacrylate (PMMA) plates were used and were roughened on one side to a three-dimensional surface topography of 5 micrometers.

Table 1 lists the compositions of 3 creams that were tested.

TABLE 1

| Cream #1 (comparative) | Base cream without microparticles. |
|---|---|
| Cream #2 (comparative) | Base cream with 5 w/w % of cellulose microparticles (without $TiO_2$), prepared as described above in the present example. |
| Cream #3 | Base cream with 5 w/w % of cellulose microparticles containing 20 w/w % of $TiO_2$ nanoparticles, prepared as described above in the present example. |

The base cream had a pH of 4.5 and comprised the following ingredients: water, 1,3-butylene glycol, isonosyl isononanoate, dimethicone, cetyl alcohol, glyceryl stearate, PEG-75 stearate, ceteth-20, steareth-20, ammonium acryloyldimethyllaurate/VP copolymer, phenoxyethanol, DL-alpha-tocopheryl acetate, sodium citrate, and sodium benzoate.

The SPF values of these creams were determined as follows.

Four measurements of spectral irradiance transmitted for each wavelength through a poly(methylmethacrylate) (PMMA) plate covered with the sunscreen product were obtained after pre-irradiation of the sunscreen product Cream #1, Cream #2, and Cream #3. For each test product, mean absorbance values were determined from two PMMA plates.

The results are listed in Table 2.

TABLE 2

| | Critical Wavelength (nm) | SPF |
|---|---|---|
| Cream #1 (comparative) | 392 | 1.1 |
| Cream #2 (comparative) | 389 | 1.9 |
| Cream #3 | 384 | 4.2 |

The nanotitanium dioxide nanoparticles in the resulting hybrid CNC-nanotitanium dioxide microparticle imparted an SPF booster effect. They also affected the transparency and a whitening effect. This is illustrated in Table 2 and in FIG. 13.

Example 9: IR Spectra of CNC Microparticles

Figure 15:
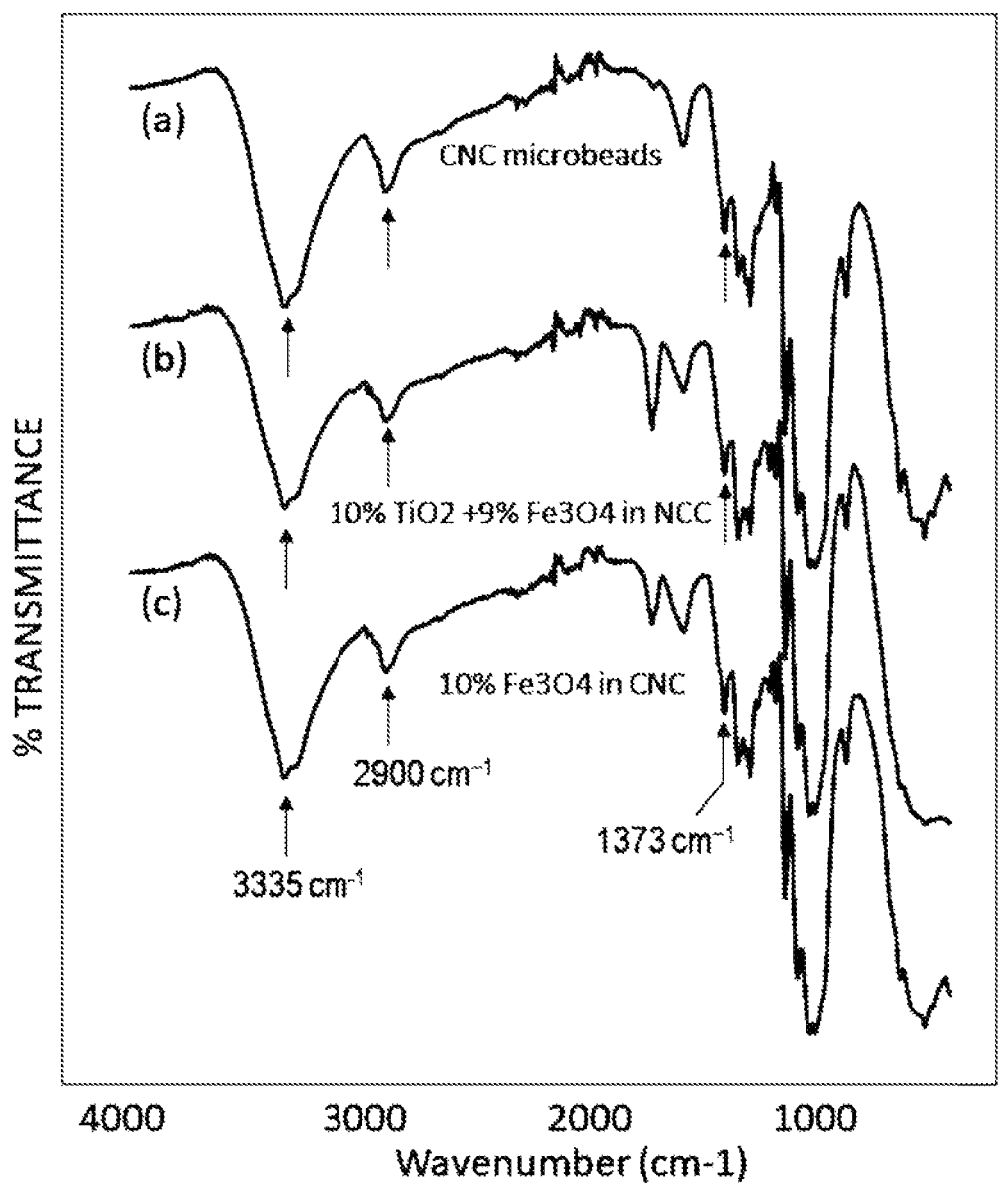
FIG. 15 (a) shows the infrared spectrum of CNC compared with (b) the infrared spectrum of 10% $TiO_2$+9% $Fe_3O_4$ in CNC compared with (c) the infrared spectrum of 10% $Fe_3O_4$ in CNC.

In this Example, infrared spectroscopy was performed on CNC microparticles (or microbeads) with no $TiO_2$ or $Fe_3O_4$ (FIG. 15(a), comparative example), CNC microparticles with 10% $TiO_2$ and 9% $Fe_3O_4$ (FIG. 15 b(b)), and CNC microparticles with 10% $Fe_3O_4$ (FIG. 15(c)). These particles were made in the same manner as described in Examples 1-3 and 8.

Infrared spectroscopy gives additional insight into the mode of bonding between a metal oxide and a CNC surface (discussed in a previous section). In the absence of surface bound metal oxide, the infrared spectrum of CNC (FIG. 15 a) shows absorptions in the following regions: characteristic cellulose bands at 667, 615, 559 cm-1, COH: out-of-plane bending; 898 cm-1, COC stretching at β-(1→4)-glycoside linkages; 1032, 1059 cm-1, CO at C6 and CC stretching; 1113, 1165 cm-1, COC stretching at β glycoside linkages; 1236 cm-1, COH in plane bending at C6; 1319 cm-1, CH2 rocking vibration at C6; 1373 cm-1, CH in plane bending; 1427 cm-1, HCH in-plane bending vibration, CH2 scissoring motion, CH2 symmetric bending at C6; 1647 cm-1, OH bending of absorbed water; 1730 cm-1 assigned to C=O stretching of carboxyl of carboxylic acid (or shifted to 1600 cm-1 and assigned to C=O stretching of carboxyl of carboxylate salt); 2899 cm-1, CH symmetrical stretching; 3400-3368 cm-1, OH intra H-bond and inter-O (3)H—O(5) bond. Bands located at 1427 and 1373 cm-1 and the one at 837 cm-1 correspond to CNC crystalline and amorphous domains, respectively.

Formation of hydrogen bonds between oxides and polysaccharides is typically indicated by shifts in absorption in the OH stretching region to a lower wavenumber. This shift can be used to measure the interaction between the adsorbed metal oxide and the CNC.

FIG. 15 (a) shows the stretching region of the CNC microsphere surface hydroxyl. FIGS. 15 (b) and (c) show that the spectral region is broadened on the low wavenumber side when the microspheres are combined with $TiO_2/Fe_3O_4$ (b) and with (nominally) magnetite ($Fe_3O_4$) (c).

The interaction with the oxides and the CNC surface is put in more quantitative terms by examining the asymmetry ratio of the widths of the left and right side of the peak centered near 3335 cm-1. The asymmetry ratio is calculated as the full width at half-maximum of the absorption band, (A/B). When the number of hydroxyl groups involved in weak and strong hydrogen bonds is the same, the asymmetry coefficient is close to 1, which is typical for unmodified cellulose materials. CNC microspheres containing no metal oxide yield a ratio of 1.06, close to theoretical unity. When 10% magnetite is bound to the microsphere the ratio is 0.68. When 9% magnetite is bound together with 10% TiO2 to the CNCs in the microsphere the ratio is 0.81. These data show that the metal oxides interact by hydrogen bonding with the CNC host.

As mentioned previously, binding of a metal oxide to CNC can reduce the crystallinity index of the nanocrystal, expressed as percent crystallinity, and this is especially the case when ultrasound is used to disperse and distribute the metal oxide. The crystallinity index can be determined by infrared spectroscopy by taking the ratio of the intensity of absorption bands located near or at 1370 cm-1 and at 2900 cm-1 (FIG. 15 a-c). The crystallinity index determined this way for CNC microspheres with no added metal oxide is determined to be approximately 82%, a value that is similar to that when measured by powder x-ray diffraction. The crystallinity index when 10% Fe3O4 is bound to the CNC microsphere falls to approximately 75%. The crystallinity index of 10% TiO2 mixed with 9% Fe3O4 in the CNC microbead is approximately 71%. Therefore, binding of magnetite and magnetite/TiO2 particles to a CNC microsphere reduces the crystallinity index of the CNC.

From the above results, it is clear that using CNCs combined with pigment nanoparticles produces microparticles of CNCs with pigment nanoparticles bound thereto, and that these microparticles can make for effective pigments.

The scope of the claims should not be limited by the preferred embodiments set forth in the examples, but should be given the broadest interpretation consistent with the description as a whole.

REFERENCES

The present description refers to a number of documents, the content of which is herein incorporated by reference in their entirety. These documents include, but are not limited to, the following:
WO 2016\015148 A1
WO 2017/091893
"Refractive index functions of TiO2 nanoparticles", S. Auvinen et al., J. Phys. Chem. C, vol. 117, pp. 3503-3512, 2013
K. Davis et el, "Quantitative Measurement of Ligand Exchange on Iron Oxides via Radiolabeled Oleic Acid", Langmuir 2014, 30, 10918-10925; dx.doi.org/10.1021/1a502204g
Markova et al., "Surface Modification of TiO2 Nanoparticles for Photochemical Reduction of Nitrobenzene", Environ. Sci. Technol. 2000, 34, 4797-4803
Moser et al., "Surface Complexation of Colloidal Semiconductors Strongly Enhances Electron Transfer Rates", Langmuir 1991, 7, 3012-8;
S. Tunesi, "Influence of Chemisorption on the Photodecomposition of Salicylic Acid and Related Compounds Using $TiO_2$ Suspended Ceramic Membranes" J. Phys. Chem. 1991, 95, 3399-405
I. Martakov et al., "Interaction of cellulose nanocrystals with titanium dioxide and peculiarities of hybrid structures formation", J Sol-Gel Sci Technol (2018) 88:13-21; I. Levdik et al., IR study of analytical and structural characteristics of low substituted methylcellulose films. J Appl Spectrosc 3:269-272(1965)
Markatov et al. (op. cit, vide supra)
C. Bohren and D. Huffman, Absorption and Scattering of Light by Small Particles, 1983 by John Wiley & Sons, Inc.

The invention claimed is:

1. A microparticle comprising carboxylated, sulfated, or phosphated cellulose nanocrystals and pigment nanoparticles, wherein the cellulose nanocrystals and the pigment nanoparticles are agglomerated together thereby forming said microparticle, and wherein the pigment nanoparticles are bound directly to the surface of the cellulose nanocrystals by covalent bonding or noncovalent bonding selected from hydrogen bonding, ionic bonding, van der Waals interactions, hydrophobic interactions and combinations thereof, and without using polyelectrolyte.

2. The microparticle of claim 1, wherein the cellulose nanocrystals are carboxylated cellulose nanocrystals.

3. The microparticle of claim 1, wherein the pigment nanoparticles are present in an amount of between about 0.1 wt % and about 75 wt % of the combined weight of the pigment nanoparticles and the cellulose nanocrystals.

4. The microparticle of claim 1, wherein the pigment nanoparticles are inorganic pigment nanoparticles, organic pigment nanoparticles, or a mixture thereof.

5. The microparticle of claim 1, wherein the pigment nanoparticles are organic pigment nanoparticles.

6. The microparticle of claim 5, wherein organic pigment nanoparticles are nanoparticles of least one of FD&C Blue 1 Aluminum Lake, D&C Blue 4 Aluminum Lake, D&C Green 3 Aluminum Lake, D&C Orange 4 Aluminum Lake, D&C Orange 5 Aluminum Lake, D&C Orange 5 Aluminum/Zirconium Lake, D&C Orange 5 Zirconium Lake, D&C Red 4 Aluminum Lake, D&C Red 6 Barium Lake, D&C Red 6 Aluminum Lake, D&C Red 6 Barium/Strontium Lake, D&C Red 6 Potassium Lake, D&C Red 6 Strontium Lake, D&C Red 7 Barium Lake, D&C Red 7 Aluminum Lake, D&C Red 7 Calcium/Strontium Lake, D&C Red 7 Zirconium Lake, D&C Red 7 Strontium Lake, D&C Red 21 Aluminum Lake, D&C Red 27 Aluminum Lake, D&C Red 27 Aluminum/Titanium/Zirconium Lake, D&C Red 27 Barium Lake, D&C Red 27 Calcium Lake, D&C Red 27 Zirconium Lake, D&C Red 28 Al Lake, D&C Red 30 Aluminum Lake, D&C Red 30 Talc Lake, D&C Red 33 Aluminum Lake, D&C Red 34 Aluminum Lake, D&C Red 36 Aluminum Lake, D&C Red 36 Zirconium Lake, F&DC Red 40 Aluminum Lake (Allura Red), F&DC Red 40 Calcium Lake, FD&C Yellow 5 Aluminum Lake, FD&C Yellow 5 Zirconium Lake, FD&C Yellow 6 Aluminum Lake, or D&C Yellow 10 Aluminum Lake.

7. The microparticle of claim 1, wherein the pigment nanoparticles are inorganic pigment nanoparticles.

8. The microparticle of claim 7, wherein the inorganic pigment nanoparticles are metal oxide nanoparticles.

9. The microparticle of claim 7, wherein the inorganic pigment nanoparticles are nanoparticles of an iron oxide, a chromium oxide, an ultramarine, a manganese pigment, or a titanium dioxide.

10. The microparticle of claim 7, wherein the inorganic pigment nanoparticles are titanium dioxide nanoparticles, black magnetite ($Fe_3O_4$) nanoparticles, or ultramarine nanoparticles.

11. The microparticle of claim 7, wherein the inorganic pigment nanoparticles are black magnetite nanoparticles.

12. The microparticle of claim 11, wherein the black magnetite nanoparticles have a particle size between about 10 nm and about 500 nm in size.

13. The microparticle of claim 11, wherein the black magnetite nanoparticles have a surface area of greater than 60 $m^2$/g.

14. The microparticle of claim 11, wherein the black magnetite nanoparticles are at a concentration from about 0.1% w/w to about 50% w/w, based on the combined weight of the cellulose nanocrystals and the black magnetite nanoparticles.

15. The microparticle of claim 1, further comprising dyed cellulose nanocrystals of at least one hue, the dyed cellulose in admixture with said nanocrystals having pigment nanoparticles bound directly to the surface of the cellulose nanocrystals.

16. The microparticle of claim 15, wherein the dyed cellulose nanocrystals comprise:
cellulose nanocrystals having a surface charge,
optionally one or more polyelectrolyte layers with alternating charges adsorbed on top of each other on the cellulose nanocrystals, the polyelectrolyte layer closest to the cellulose nanocrystals having a charge opposite the surface charge of the cellulose nanocrystals, and
at least one organic dye having a charge,
wherein:
A) when the charge of the organic dye is opposite the surface charge of the cellulose nanocrystals,
  1) The organic dye is directly adsorbed on the surface of the cellulose nanocrystals without intervening polyelectrolyte layers, or
  2) the organic dye is adsorbed on an even number of polyelectrolyte layers with alternating charges, and
B) when the charge of the organic dye is the same as the surface charge of the cellulose nanocrystals, the organic dye is adsorbed on an odd number of polyelectrolyte layers with alternating charges.

17. The microparticle of claim 15 wherein the dyed cellulose nanocrystals comprise Citrus red 2, FD&C Blue 1, D&C Blue 4, D&C Green 3, D&C Green 4, D&C Green 5, D&C Green 6, D&C Green 8, D&C Orange 4, D&C Orange 5, D&C Orange 10, D&C Orange 11, FD&C Red 4, D&C Red 6, D&C Red 7, D&C Red 21, D&C Red 27, D&C Red 28, D&C Red 30, D&C Red 31, D&C Red 33, D&C Red 34, D&C Red 36, D&C Red 39, FD&C Red 40, D&C Red 40, D&C Violet 2, FD&C Yellow 5, FD&C Yellow 6, D&C Yellow 10.

18. A cosmetic preparation comprising the microparticles of claim 1.

19. A method for producing the microparticles of claim 1, the method comprising the steps of:
  a. producing an aqueous suspension of the carboxylated, sulfated, or phosphated CNCs with pigment nanoparticles bound thereto; and
  b. drying said aqueous suspension to produce the microparticles.

20. The method of claim 19, wherein step a) comprises the steps of producing an aqueous suspension of the carboxylated, sulfated, or phosphated CNCs and then adding the pigment nanoparticles to the aqueous suspension.

21. The method of claim 19, wherein step b) comprises spray-drying the suspension.

* * * * *